(12) United States Patent
Becker et al.

(10) Patent No.: US 11,390,851 B2
(45) Date of Patent: Jul. 19, 2022

(54) PROCESS FOR GENERATION, IDENTIFICATION AND ISOLATION OF HUMAN PLURIPOTENT STEM CELL-DERIVED CARDIOMYOCYTES AND CARDIOMYOCYTE SUBPOPULATIONS

(71) Applicant: Miltenyi Biotec GmbH, Bergisch Gladbach (DE)

(72) Inventors: Kristin Becker, Bergisch Gladbach (DE); Dominik Eckardt, Bergisch Gadbach (DE); Andreas Bosio, Cologne (DE)

(73) Assignee: Miltenyi Biotec B.V. & Co. KG, Bergisch Gladbach (DE)

( * ) Notice: Subject to any disclaimer, the term of this patent is extended or adjusted under 35 U.S.C. 154(b) by 723 days.

(21) Appl. No.: 16/305,364

(22) PCT Filed: May 30, 2017

(86) PCT No.: PCT/EP2017/063047
§ 371 (c)(1),
(2) Date: Nov. 28, 2018

(87) PCT Pub. No.: WO2017/207576
PCT Pub. Date: Dec. 7, 2017

(65) Prior Publication Data
US 2020/0318072 A1  Oct. 8, 2020

(30) Foreign Application Priority Data
Jun. 1, 2016  (EP) .................... 16172528

(51) Int. Cl.
*A61K 35/34* (2015.01)
*C12N 5/077* (2010.01)
*G01N 33/50* (2006.01)
*G01N 33/58* (2006.01)

(52) U.S. Cl.
CPC ............ *C12N 5/0657* (2013.01); *A61K 35/34* (2013.01); *G01N 33/5005* (2013.01); *G01N 33/582* (2013.01); *C12N 2501/115* (2013.01); *C12N 2501/155* (2013.01); *C12N 2501/16* (2013.01); *C12N 2501/999* (2013.01); *C12N 2506/02* (2013.01); *C12N 2506/45* (2013.01)

(58) Field of Classification Search
None
See application file for complete search history.

(56) References Cited

U.S. PATENT DOCUMENTS

2015/0160237 A1 * 6/2015 Wiencierz ............... C12N 5/00
424/93.7

FOREIGN PATENT DOCUMENTS

| WO | WO-2009072003 | A2 * | 6/2009 | ........... B03C 1/0332 |
| WO | WO 2012133954 | | 10/2012 | |
| WO | WO 2012135253 | | 10/2012 | |
| WO | WO-2012135253 | A1 * | 10/2012 | ........... C12N 5/0657 |
| WO | WO 2014014119 | | 1/2014 | |
| WO | WO-2014014119 | A1 * | 1/2014 | ........... C12N 5/0657 |

OTHER PUBLICATIONS

Wiencierz (PLOS One, 10(11): e0143538. p. 1-20, 2015, (Year: 2015).*
Dubois, et al., "SIRPA is a specific cell-surface marker for isolating cardiomyocytes derived from human pluripotent stem cells," Nature Biotechnology, 2011, 29(11):1011-1018.
International Search Report and Written Opinion in PCT Appln. No. PCT/EP2017/063047, dated Aug. 23, 2017, 15 pages.
Xu, "Differentiation and enrichment of cardiomyocytes from human pluripotent stem cells," J. Mol. Cell. Cardiol., 2012, 52(6):1203-1212.

* cited by examiner

*Primary Examiner* — Anoop K Singh
*Assistant Examiner* — Magdalene K Sgagias
(74) *Attorney, Agent, or Firm* — Fish & Richardson P.C.

(57) ABSTRACT

The present invention provides a method for generation, isolation, detection and/or analysis of cardiomyocytes derived from a starting cell composition comprising pluripotent and/or multipotent stem cells, the method comprising the steps a) differentiating said pluripotent and/or multipotent stem cells into cardiovascular cells, thereby generating a sample comprising cardiomyocytes and non-cardiomyocytes; and b) labeling the non-cardiomyocytes of said sample with more than one antibody or antigen binding fragment thereof specific for antigens of non-cardiomyocytes and c) depleting said labeled non-cardiomyocytes from said sample; and optionally d) labeling the cardiomyocytes of said sample with at least one antibody or antigen binding fragment thereof specific for antigen(s) of cardiomyocytes; and e) enriching said labeled cardiomyocytes and detecting and isolating cardiomyocyte subtypes derived from said pluripotent and/or multipotent stem cells.

11 Claims, 26 Drawing Sheets

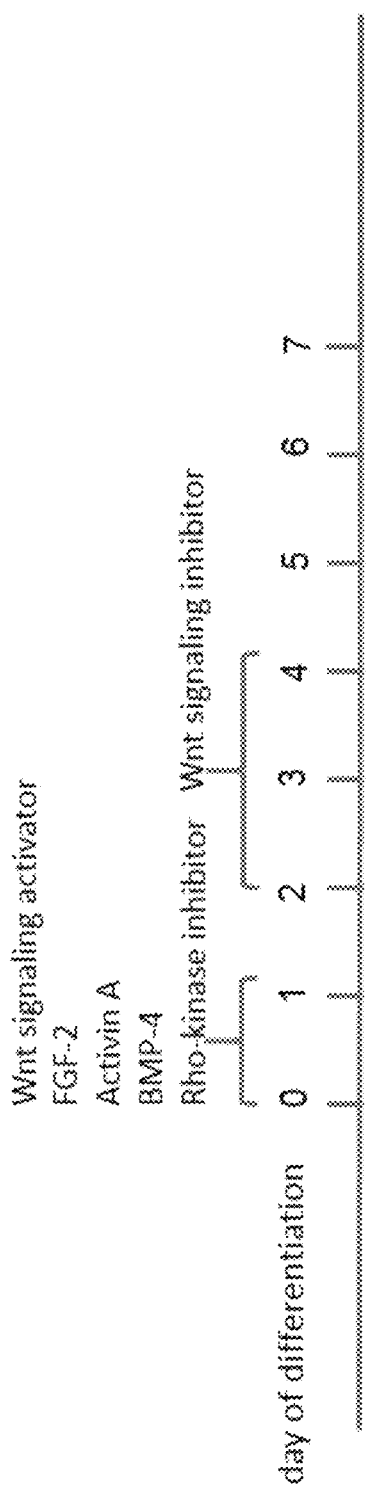
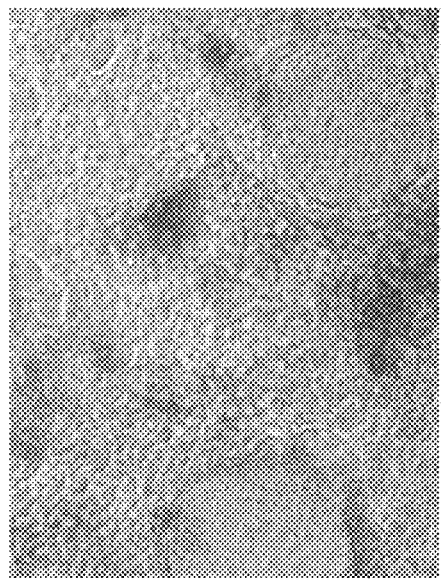
FIGURE 1A
FIGURE 1C
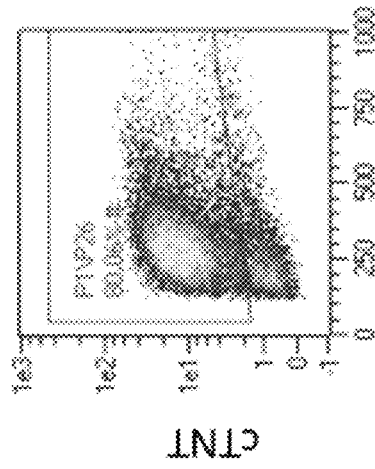
FIGURE 1B

PROCESS FOR GENERATION, IDENTIFICATION AND ISOLATION OF HUMAN PLURIPOTENT STEM CELL-DERIVED CARDIOMYOCYTES AND CARDIOMYOCYTE SUBPOPULATIONS

CROSS REFERENCE TO RELATED APPLICATIONS

The present application is the national stage entry of International Patent Application No. PCT/EP2017/063047, filed on May 30, 2017, and claims priority to Application No. EP 16172528.8, filed in on Jun. 1, 2016, the disclosures of which are incorporated herein by reference.

BACKGROUND

Cardiovascular diseases are the major cause of death worldwide. After cardiac infarction a high number of cardiomyocytes (CM) is lost and replaced by fibroblasts forming scar tissue. This leads to arrhythmias and reduced heart function. Therefore, a high need exists for effective cell replacement strategies. For that reason the generation of pure and well-characterized human pluripotent stem cell (PSC) derived cardiomyocytes is a pre-requisite. Moreover, for cell replacement therapies a huge amount of cardiomyocytes (>10E9 cells/dose) is needed and to date no scalable, fully automated cardiac differentiation and purification process is available. Several methods have been described for the in vitro generation of PSC-derived cardiomyocytes generating a mixture of target cells (cardiomyocytes) and non-target cells (non-cardiomyocytes) to different extent, depending e.g. on the differentiation protocol or the stem cell line used. Protocols described so far are mainly based on manual cell processing procedures using various basal media and cytokine/small molecule compositions. Most protocols include the activation and inhibition of Wnt signalling, some protocols use Activin A and BMP4 as additional regulators. For example, US20140134733A1 and EP14167201.4 describe a broadly used protocol based on use of Wnt agonists and antagonists, including e.g. B27 supplement (not xeno-free), making it less applicable for regenerative medicine approaches. A highly complex protocol using a variety of cytokines and small molecules is disclosed in US20140193909A1. Although high differentiation efficiencies were described, the protocol is difficult to standardize due to the complexity of the media formulations and expected variabilities of differentiation efficiencies between various stem cell clones. WO2013063305A2 discloses a differentiation protocol that enables the generation of cardiomyocytes under defined conditions. The protocol includes blebistatin, Activin A, BMP-4 and IWR-1 in combination with the basal medium StemPro 34® (Life Technologies). It is claimed to obtain differentiation efficiencies of >90% after 21 days in culture. However, harvesting of stem cells prior to differentiation induction is described using dispase leading to formation of cell clumps. Cell numbers cannot be determined, making the initial cell seeding complicated and less controllable or standardized. For this reason and because of the relatively long differentiation times this protocol seems to be less applicable for regenerative medicine approaches. In 2015 a similar protocol was published which includes additionally to the small molecules mentioned above CHIR99021 (a GSK3 inhibitor), Wnt-059 (a Wnt signaling inhibitor) and KO DMEM as basal medium (Zhang et al., 2015). High differentiation efficiencies were achieved within 8 days of differentiation.

Cardiovascular differentiations of human PSC cultures do not contain homogeneous cell populations, but are rather composed of a variety of cardiomyocytes and non-cardiomyocytes as well as cardiomyocyte subtypes or subpopulations. Importantly, impurity or heterogeneity of hPSC-derived cardiomyocyte populations will affect any kind of downstream application, e.g. cellular therapies. If target and non-target cells or mixtures of cardiomyocyte subpopulations are transplanted cardiac arrhythmias might be induced. Several methods have been described for the isolation of PSC-derived cardiomyocytes including metabolic selection, genetic engineering or surface marker-based separation:

Tohyama et al. (2013) and US20090275132A1 described metabolic selection of cardiomyocytes based on lactate supplementation of the medium. Although the method intends selective killing of non-myocytes, proliferating cardiomyocytes are affected as well, thereby giving low recoveries of cardiomyocytes. Additionally, the metabolic selection is a long-term process and needs to be carried out over several days.

Enrichment of PSC-derived cardiomyocytes can as well be achieved by genetic manipulation and antibiotic selection (Xu et al., 2008). Even though almost pure cardiomyocyte cultures can be obtained by antibiotic selection, lack of genetic modifications is favoured for cell therapeutic approaches.

Surface marker-based enrichment of PSC-derived cardiomyocytes has also been described, e.g. using Sirpa or VCAM-1-based cell separation protocols (Dubois et al., 2011, Uosaki et al., 2011). However, these markers were shown to only partially label CMs and additionally non-cardiomyocytes and are therefore unsuitable for the establishment of standardized cardiomyocyte purification processes needed for cell therapeutic developments. In addition high loss of cardiomyocytes during magnetic enrichment using antibodies against VCAM-1 or Sirpa were described (e.g. Fuerstenau-Sharp et al., 2015).

US2015/0184129 A1 discloses CD340, CD56, SSEA-3 and SSEA-4 as cardiomyocyte specific markers. Antibodies against these antigens are described to allow for enrichment of cardiomyocytes from mixed cell populations of cardiomyocytes and non-cardiomyocytes without prior removal of non-cardiomyocytes. Nevertheless, all markers are well known to be expressed on non-cardiomyocytes as well, e.g. neural cells or NK cells (CD56) or epithelial and pluripotent stem cells (CD340, SSEA-3, SSEA-4). Therefore, selective purification of cardiomyocytes generated by cardiovascular differentiation of pluripotent stem cells is very unlikely without a previous purification step, enabling the removal of relevant non-cardiomyocyte populations.

Moreover, it was reported that PSC cultures differentiated towards the cardiac lineage also comprise non-cardiomyocytes positive for CD90, CD31, CD140b and CD49a (e.g. Dubois et al., 2011). As suggested by Dubois et al. (2011) an approach of removing cells expressing these markers can be used for enrichment of cardiomyocytes. WO2012/135253A1 and WO2012/024782A1 described methods for CM enrichment by depletion of cells positive for one or more of these markers: CD90, CD73, CD140b, CD10, CD105, CD44, Stro-1; SSEA-3, SSEA-4, Tra-1-60, Tra-1-81. Claims focus on CD90 as the most important marker of non-cardiomyocytes.

Additionally, it is known that PSC-derived cardiomyocyte populations contain mixtures of cardiomyocyte subpopulations e.g. atrial-, ventricular-, and pacemaker-like cells as well as different maturity stages as previously shown e.g. by electrophysiological characterisation of respective cell cultures (e.g. Burridge et al., 2014). To date, only few markers have been described that might enable for the identification or selective isolation of cardiac progenitors, e.g. CD13 and ROR2 (Skelton et al., 2016). Data from expression profiling of PSC-derived cardiomyocytes could not yet be translated into cell identification or cell separation procedures aiming at the enrichment of cardiomyocyte subpopulations (Piccini et al., 2015; van den Berg et al., 2015).

In more detail, current limitations of cardiomyocyte purification protocols are:

a. lack of cardiomyocyte marker specificity, e.g. by use of surface antibodies labeling cardiomyocytes and non-myocytes (Sirpa- and VCAM-1 based CM purification strategies)

b. high loss of cardiomyocytes during the isolation procedure, e.g. by magnetic cell separation (Dubois et al., 2011; Fuerstenau-Sharp et al., 2015) or lactate-based differentiation/selection media c. long-term procedures (e.g. lactate-based differentiation media) (Tohyama et al., 2013)

d. missing potential for standardization, e.g. as expression of surface markers on cardiomyocytes is subject to variations during the differentiation process and expression of surface markers on cardiomyocytes differs between differentiation protocols e. impact on cardiomyocyte function or viability f. no automated process of cardiomyocyte differentiation and purification has been established in order to standardize the procedure of cardiomyocyte production and to obtain high cell numbers required for cell replacement therapies g. currently, mixtures of cardiomyocyte subpopulations are used e.g. for pre-clinical cell therapeutic applications, and a throughout description of CM subpopulations generated by differentiation of PSCs into cardiomyocytes is missing.

Therefore, a high need exists for an improved or alternative method for generation, identification and/or isolation of human pluripotent stem cell-derived cardiomyocytes and cardiomyocyte subpopulations which e.g. subsequently allow the use of said cardiomyocytes and/or cardiomyocyte subpopulations in research, diagnostics, pharmacological and/or clinical applications, e.g. cellular therapy.

SUMMARY OF THE INVENTION

Unexpectedly, it was found that a 1- or 2-step cell separation procedure allows for robust and standardized purification (enrichment or isolation) of pluripotent stem cell derived cardiomyocytes with purities of up to 98%. The cell separation procedure developed ensures for similar purities of cardiomyocytes, independent of variations in marker gene expression and differentiation efficacies as well as the differentiation protocol and pluripotent stem cell clone used or the time point of differentiation chosen for enrichment of pluripotent stem cell derived cardiomyocytes. The cell separation procedure includes for the 1-step separation the combination of at least two antibodies or antigen binding fragments thereof against non-cardiomyocyte markers for depletion of non-cardiomyocyte, the non-cardiomyocyte markers selected from the group consisting of antiCD10, antiCD105, antiCD140b, antiCD61, antiCD44, antiCD141, and antiCD51/61. Surprisingly, the use of a combination of two of these non-cardiomyocyte markers for depletion of non-cardiomyocytes from a sample comprising cardiomyocytes derived from in vitro differentiated pluripotent and/or multipotent stem cells allows for standardization of the cardiomyocyte purification process not achieved by methods known in the art as the cell separation procedure developed ensures for similar purities of cardiomyocytes, independent of variations in marker gene expression and differentiation efficacies as well as the differentiation protocol and pluripotent stem cell clone used or the time point of differentiation chosen for enrichment of pluripotent stem cell derived cardiomyocytes. Robustness of this cell separation procedure allows for transfer of this process to automated cell processing systems, thereby covering controlled and standardized enrichment of high cell numbers of cardiomyocytes as required e.g. for regenerative therapy approaches.

Additionally, outstanding purities and recoveries of the enriched cell composition of cardiomyocytes are obtainable that are not achieved by methods known in the art. The addition of one or more non-cardiomyocyte markers selected from said group of non-cardiomyocyte markers to said two-marker-combinations leads to further of the purities and/or recoveries of cardiomyocytes in the generated cell composition of cardiomyocytes (FIGS. 7-11). Importantly, the combination of at least two of said non-cardiomyocyte markers is sufficient two deplete all types of cells that are not cardiomyocytes but would be labeled by an antibody selected for the cardiomyocyte enrichment step after depletion of non-cardiomyocytes, i.e. that lead to the depletion of undesired (non-target) cells from the sample. The depletion of the non-cardiomyoctes using more than one of said non-cardiomyocyte markers is independent of any possible contaminating cells of the starting cell composition comprising pluripotent and/or multipotent stem cells if this cell population is differentiated into cardiomyocytes by methods known to a person skilled in the art.

A preferred cell separation procedure includes for the 1-step separation the combination of antibodies against non-cardiomyocyte markers, CD140b, CD141, CD10 for depletion of non-cardiomyocytes. The 2-step separation procedure includes depletion of non-cardiomyocytes by using the non-cardiomyocyte makers as disclosed herein and the combinations of the antibodies or antigen binding fragments thereof as disclosed herein as well as a subsequent or simultaneous cardiomyocyte enrichment step with at least one antibody or antigen binding fragment thereof selected from the group consisting of antiPTK7, antiCD99, antiCD276, antiCD56, antiCD59, antiCD147, antiCD239, antiCD298, antiCD49f, antiCD262, antiCD81, antiTra-1-85, antiCD49e, antiCD24, antiCD47, antiCD46, antiCD49c, antiCD51, antiCD29, antiCD98, antiCD63, antiCD146c, and antiCD151. Preferentially, the cardiomyocyte marker is CD56.

A preferred 2-step separation procedure includes depletion of non-cardiomyocytes by a combination of antibodies against CD140b, CD141 and CD10 as well as a subsequent or simultaneous cardiomyocyte enrichment step with an antibody against CD56.

Additionally, novel cell surface markers were identified enabling for identification and subsequent purification of cardiomyocyte subpopulations from previously enriched pluripotent stem cell derived cardiomyocytes by magnetic or fluorescence activated cell sorting. Functionality of each subpopulation identified might outperform the mixture of cardiomyocyte subpopulations currently used e.g. for the development of cell therapeutic applications. Cardiomyocytes generated by differentiating pluripotent or multipotent stem cells into cardiomyocytes by methods known to a person skilled in the art, e.g. Zhang et al. (2015) or any other robust PSC cardiomyocyte differentiation protocol can be further purified by the newly developed protocols for enrichment of cardiomyocytes and cardiomyocyte subpopulations. Importantly, the newly developed procedures for enrichment of cardiomyocytes and cardiomyocyte subtypes are applicable to manual or automated magnetic as well as fluorescence activated cell sorting procedures providing highly purified pluripotent stem cell derived cardiomyocytes. Thereby the generation of pluripotent stem cell-derived cardiomyocytes and subsequent purification of cardiomyocytes and cardiomyocyte subpopulations can surprisingly be performed in a closed cell sample processing system resulting in cardiomyocytes generated under GMP or GMP-like conditions. Even more unexpectedly, it was found that the process of the present invention is accessible to an automated procedure using said closed cell sample processing system. The cells of the composition obtained by the methods of the present invention may, for example, be used in cell replacement therapies for patients as a therapeutic treatment to ameliorate or reverse symptoms caused by the loss of cardiomyocytes in a patient suffering from cardiovascular diseases associated with loss of cardiomyocytes, e.g. coronary heart disease.

BRIEF DESCRIPTION OF THE DRAWINGS

FIGS. 1A-C The protocol used for the generation of pluripotent stem cell-derived cardiomyocytes was based on a previously published method by Zhang et al. (2015), combining Wnt signaling activators and inhibitors as well as FGF-2, Activin A, BMP-4 and a Rho-kinase inhibitor (FIG. 1A). Cardiomyocytes were generated with high efficacies as shown by flow cytometry analysis of cardiac Troponin T (cTnT) expression (FIG. 1B) and the typical morphology of PSC-derived cardiomyocyte cultures (FIG. 1C).

FIG. 11A) Uptake of the calcium sensitive dye Fluo 8 by cardiomyocytes after purification and replating proves cardiomyocyte functionality. FIG. 11B) Purified and replated cardiomyocytes show a typical morphology.

FIG. 14A, FIG. 14B, FIG. 14C, FIG. 14D, FIG. 14E and FIG. 14F show potential marker combinations that can be used for the purification of PSC derived cardiomyocytes. All marker combinations show only little co-expression with the specific cardiac marker cTNT, but strong co-expression with the cTNT negative population. This qualifies them as suitable markers for a highly efficient depletion of non-cardiomyocytes. Moreover, marker combinations are co-expressed with CD56, indicating the need to remove those cells prior to enrichment of cardiomyocytes using antibodies against CD56. In all dot plots the single positive CD56 cardiomyocyte population is clearly distinguishable from the double positive CD56/non-cardiomyocte marker positive population. For that reason the single positive cardiomyocyte population can easily be sorted to get a highly pure cardiomyocyte population.

DETAILED DESCRIPTION OF THE INVENTION

We have developed novel manual as well as automated and standardized processes for the purification of cardiomyocytes derived by differentiating pluripotent and/or multipotent stem cells into cardiomyocytes by methods known to a person skilled in the art, e.g. Zhang et al. (2015), for details see FIGS. 1A-C. The purification processes are based on combinations of antibodies (more than one antibody) for the non-cardiomyocyte markers (step 1 of the method) and on single antibodies or combinations of antibodies for cardiomyocyte markers (optional step 2 of the method) identified in surface marker screenings (FIGS. 2A-B and FIGS. 3A-B) resulting in either a 1- or 2-step cell separation procedure. Following antigens specific for non-cardiomyocytes or cardiomyocytes were identified:

(i) non-cardiomyocyte markers (FIGS. 2A-B):
  CD10, CD44, CD105, CD140b, CD61, CD141, CD51/61
(ii) cardiomyocyte markers (FIGS. 3A-B):
  PTK7, CD99, CD276, CD56, CD59, CD147, CD239, CD298, CD49f, CD262, CD81, Tra-1-85, CD49e, CD24, CD47, CD46, CD49c, CD51, CD29, CD98, CD63, CD146c, CD151

Figure 4:
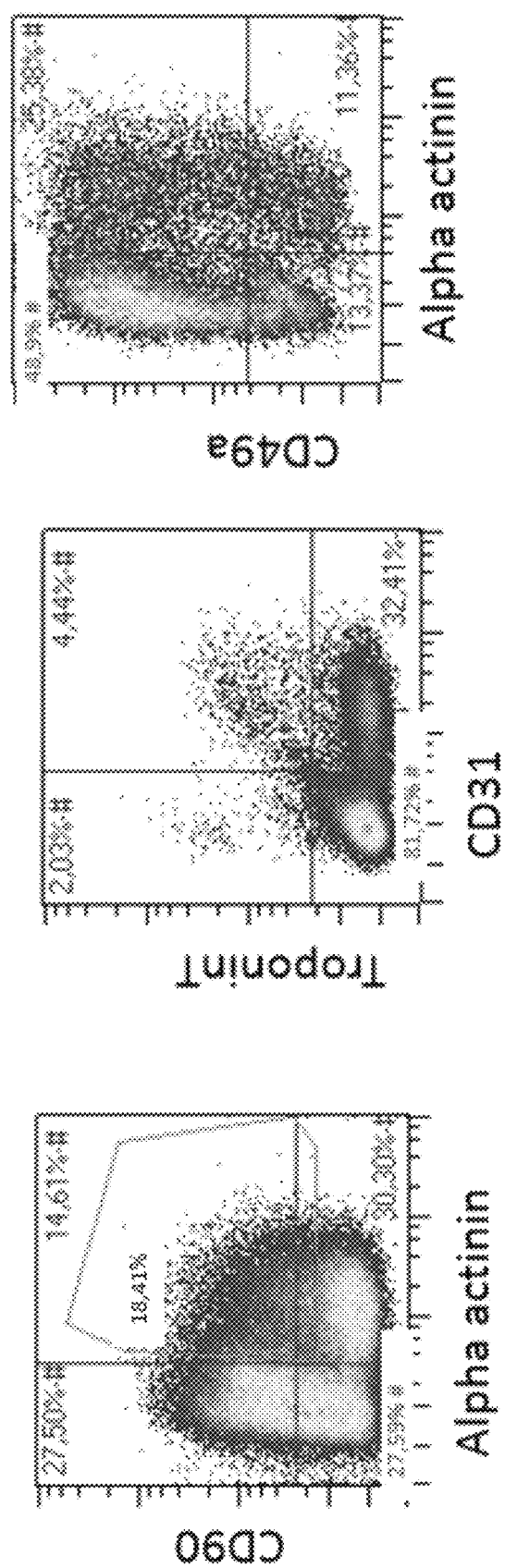
FIG. 4. Antibody-based surface marker analysis identified co-expression of several previously described non-cardiomyocyte surface markers with cardiomyocyte markers, like Alpha actinin or TroponinT, making these surface markers unsuitable for removal of non-cardiomyocytes.
Figure 5:
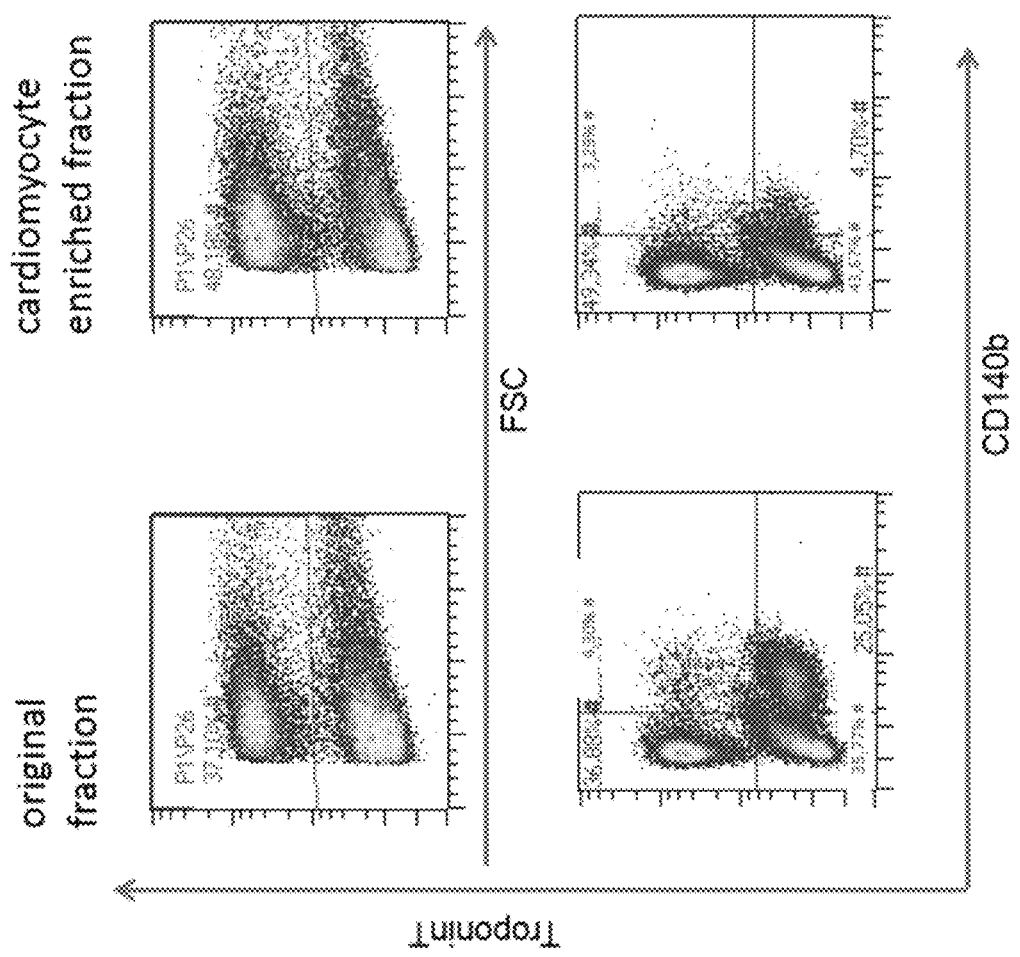
FIG. 5. Enrichment of PSC-derived cardiomyocytes by magnetic depletion of non-cardiomyocytes using antibodies against CD140b is insufficient, as the cardiomyocyte content can only be enriched from ca 37% in the original fraction to ca 48% in the cardiomyocyte enriched fraction. Cardiomyocytes are labeled by antibodies against cardiac TroponinT (cTnT).

Surprisingly, our data indicate that previously described markers for non-cardiomyocytes, like CD90, CD31 and CD49a (Dubois et al., 2011) are co-expressed with cardiomyocyte makers, like alpha actinin or cardiac Troponin T. This observation was dependent on the differentiation time point, the stem cell clone used and differentiation efficiency, making these markers unsuitable for efficient, standardized CM purification by selective removal of non-cardiomyocytes (FIG. 4). Additionally, we tested whether antibodies against a previously described marker of non-cardiomyocytes, i.e. CD140b (Dubois et al., 2011), would be sufficient for purification of cardiomyocytes by removal of non-cardiomyocytes. Our data indicate that cardiomyocytes cannot sufficiently be enriched by only using antibodies against CD140b, as the initial CM content of about 37% could only be increased to purities of ca. 48% after magnetic depletion of CD140b positive non-cardiomyocytes (FIG. 5). Furthermore, no antibody against a cardiomyocyte surface marker was found that could enable the exclusive purification of PSC derived cardiomyocytes after a CD140b-based non-cardiomyocyte depletion step. Furthermore, the amount of cells expressing CD140b is variable and dependent on differentiation efficiency, protocol and stem cell clone, thereby indicating that CD140b alone is not a suitable marker for the removal of PSC-derived non-cardiomyocytes.

Figures 6A, 6B:
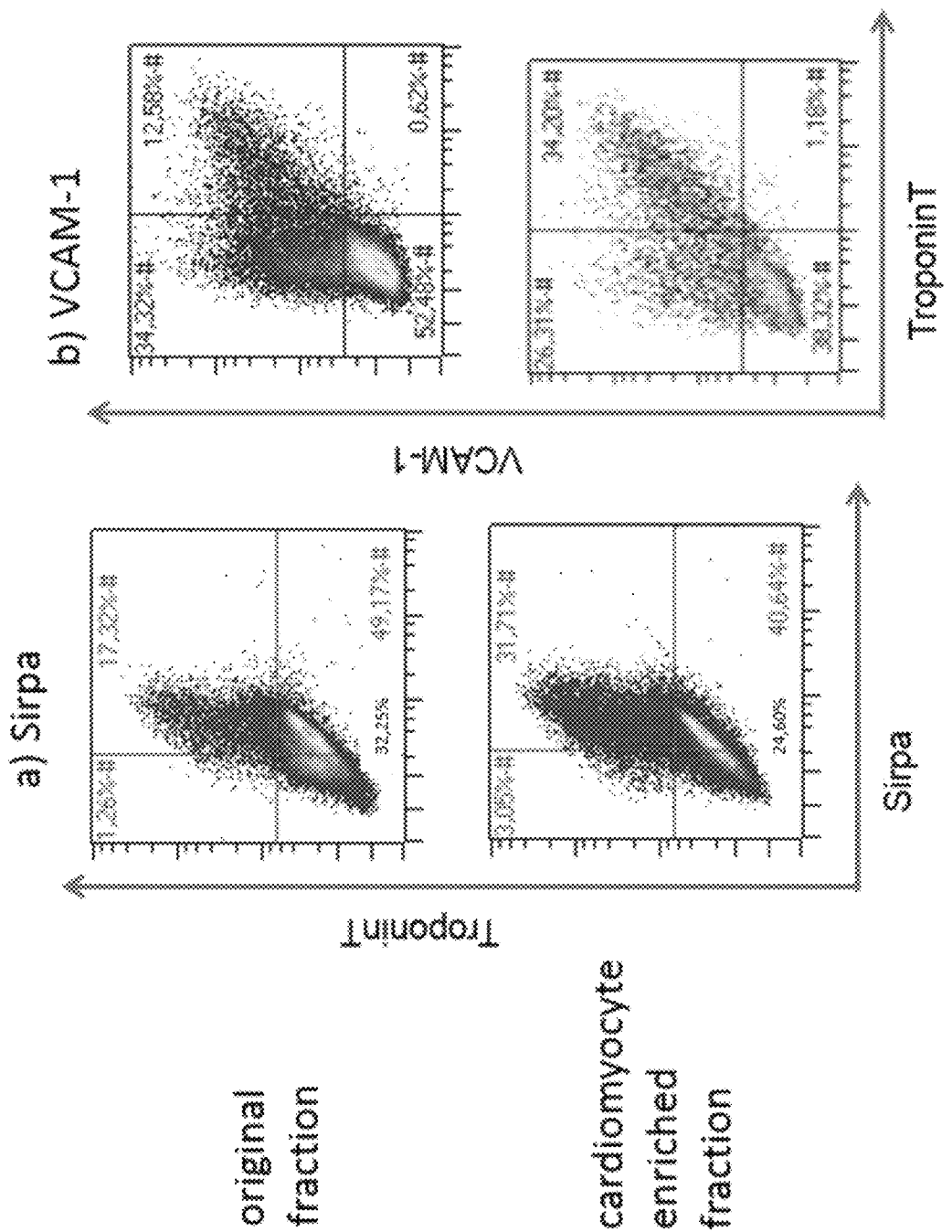
FIGS. 6A-B. Enrichment of PSC-derived cardiomyocytes by magnetic separation using antibodies against cell surface markers (FIG. 6A) Sirpa (CD172a) or (FIG. 6B) VCAM-1 (CD106). antiSirpa-based separation enriches CMs from ca 17% to ca 31%, antiVCAM-1-based separation enriches CMs from ca 12% to ca 34%. Cardiomyocytes are labeled by antibodies against TroponinT FIG. 7. Two examples for cardiomyocyte purification by magnetic cell separation using antibodies against CD140b, CD141 and CD10 for the removal of non-cardiomyocytes, i.e. 1-step procedure for cardiomyocyte purification. The dot plots show that cardiomyocytes, i.e. cardiac TroponinT (cTnT) positive cells, are enriched from ca. 66% or ca. 22% in the original fraction to purities of ca. 96% and ca. 92%, respectively.

Unexpectedly, we found that previously described surface markers for cardiomyocytes like VCAM-1 label only subpopulations of cardiomyocytes or cardiomyocytes and non-cardiomyocytes (Sirpa) and are therefore unsuitable for purification of cardiomyocytes from cardiovascular differentiations of pluripotent stem cells (FIGS. 6A-B).

Since previously described markers were unsuitable for the purification of cardiomyocytes and our screen did not lead to the identification of surface markers expressed on PSC-derived cardiomyocytes only, we developed a new method for purification of cardiomyocytes based on a 1 or 2-step procedure. Surprisingly, the new method works independently of the starting human PSC clone, the differentiation protocol used or the time point of separation (FIGS. 7-11). The process includes removal of non-cardiomyocytes in a first step and optionally a cardiomyocyte enrichment step, delivering cardiomyocytes with purities of up to 98% and very good recoveries (up to 80%).

Figure 8:
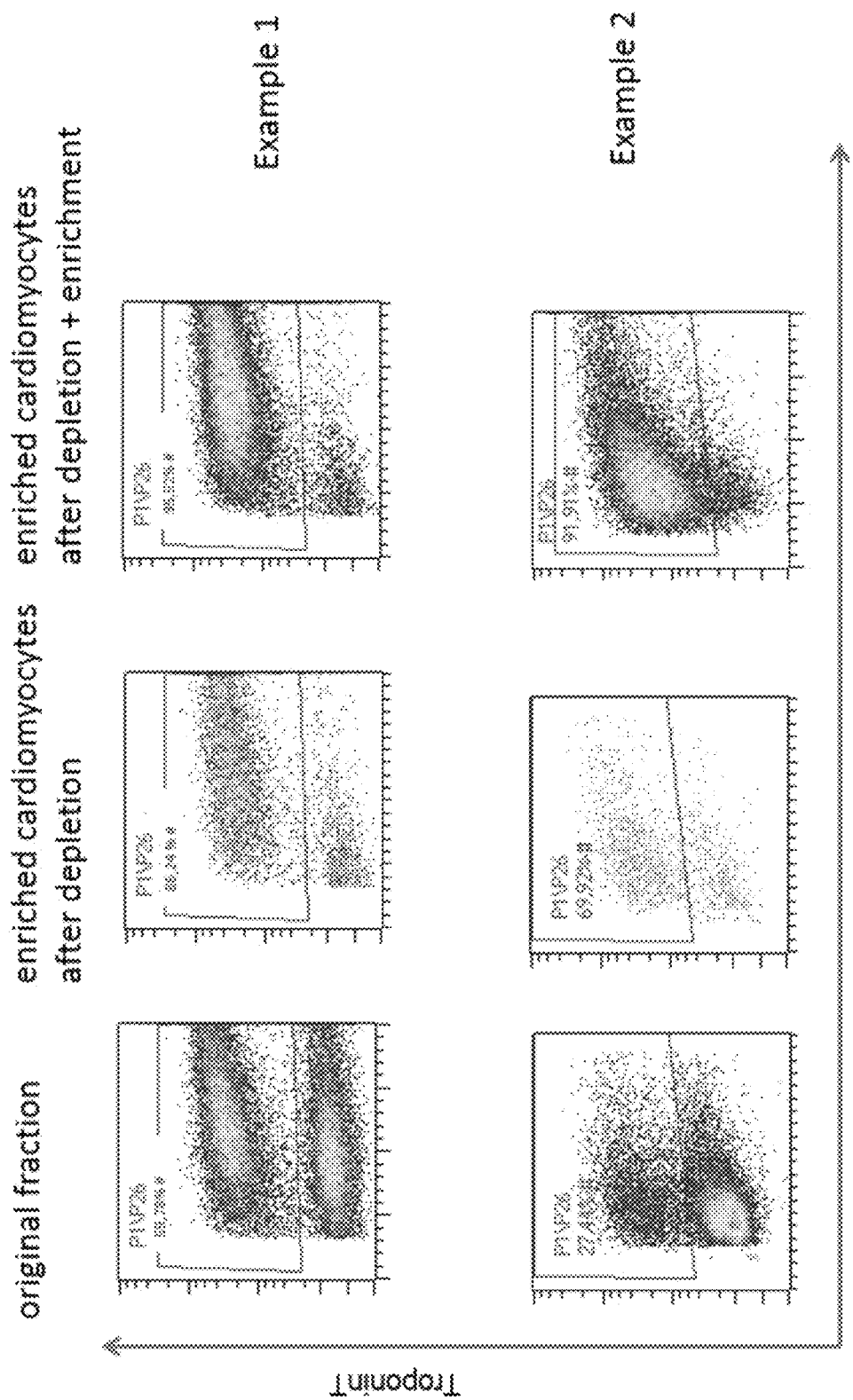
FIG. 8. Two examples for cardiomyocyte purification by subsequent depletion of non-cardiomyocytes and enrichment of cardiomyocytes by magnetic cell separation, i.e. 2-step procedure for cardiomyocyte purification. The dot plots show that cardiomyocytes, i.e. cardiac TroponinT (cTnT) positive cells, are enriched from ca 59% or ca 27% in the original fraction to purities of ca 95% and ca 92%, respectively.

Our flow cytometry-based screening identified antibodies against 7 antigens of non-cardiomyocytes that may be used in the method as disclosed herein, wherein two of these antibodies or antigen binding fragments thereof may be sufficient to deplete the non-cardiomyocytes and thereby enrich the cardiomyocytes. Such combinations of two antibodies or fragments thereof for depletion of non-cardiomyocytes as disclosed herein may be: antiCD10 and antiCD105, antiCD10 and antiCD140b, antiCD10 and antiCD61, antiCD10 and antiCD44, antiCD10 and antiCD141, antiCD10 and antiCD51/61, antiCD105 and antiCD140b, antiCD105 and antiCD61, antiCD105 and antiCD44, antiCD105 and antiCD141, antiCD105 and antiCD51/61, antiCD140b and antiCD61, antiCD140b and antiCD44, antiCD140b and antiCD141, antiCD140b and antiCD51/61, antiCD61 and antiCD44, antiCD61 and antiCD141, antiCD61 and antiCD51/61, antiCD44 and antiCD141, antiCD44 and antiCD51/61, or antiCD141 and antiCD51/61. Each of these combinations of two antibodies or antigen binding fragments thereof may be supplemented by one or more additional markers of said 7 markers (FIGS. 14A-F). A preferred combination of three antibodies or antigen binding fragments thereof may be CD140b, CD10 and CD141. But every other combination of three antibodies or antigen binding fragments thereof selected from the group of antiCD10, antiCD105, antiCD140b, antiCD61, antiCD44, antiCD141, and antiCD51/61 is also well suited for depletion as disclosed herein (FIGS. 14A-F). Either the one-step depletion of non-cardiomyocytes or the combination with a second step, enrichment of cardiomyocytes with antibodies against e.g. CD56, allowed for purification of PSC-derived cardiomyocytes by up to 98%. The 2-step procedure includes a pre-depletion step with more than one antibody or antigen binding fragment thereof selected from the group consisting of antiCD10, antiCD105, antiCD140b, antiCD61, antiCD44, antiCD141, and antiCD51/61, e.g. antibodies against CD140b, CD141, CD10 followed by enrichment of cardiomyocytes using at least one antibody or fragment thereof specific for antigen(s) of cardiomyocytes, wherein said at least one antibody or fragment thereof is selected from the group consisting of antiPTK7, antiCD99, antiCD276, antiCD56, antiCD59, antiCD147, antiCD239, antiCD298, antiCD49f, antiCD262, antiCD81, antiTra-1-85, antiCD49e, antiCD24, antiCD47, antiCD46, antiCD49c, antiCD51, antiCD29, antiCD98, antiCD63, and antiCD146c, antiCD151. For example said antibody or antigen binding fragment thereof may be an antiCD56 antibody or antigen binding fragment thereof (FIG. 8).

The antiCD56 antibody or antigen binding fragment thereof may be a preferred antibody or antigen binding fragment thereof for the positive enrichment of cardiomyocytes in step 2 of the method as disclosed herein. Since the marker CD56, chosen from the candidates identified by the surface marker screen and used for the cardiomyocyte enrichment step, is not exclusively expressed on cardiomyocytes, enrichment of cardiomyocytes to high purities with antibodies against CD56 is only possible after efficient removal of all CD56-positive non-cardiomyocytes. The combination of antibodies antiCD140b, antiCD10 and antiCD141 achieved the required removal of CD56 positive non-cardiomyocytes. Standardization of a purification protocol requires efficient coverage of variations in differentiation efficiencies and surface marker expression. The inclusion of antibodies against CD140b, CD10 and CD10 was one choice of antibody combinations to label non-cardiomyocytes and allowed for standardization of the cardiomyocyte purification protocol, i.e. giving similar purities independent of variations in marker expression or differentiation efficacies. Therefore, unexpectedly, the antibody combination enables the standardized purification of PSC derived cardiomyocytes independent from the differentiation efficiency, stem cell clone and differentiation protocol, making this purification strategy suitable for regenerative medicine applications due to robustness in performance. A similarly effective strategy for removal of non-cardiomyocytes has not yet been described elsewhere.

Figure 9:
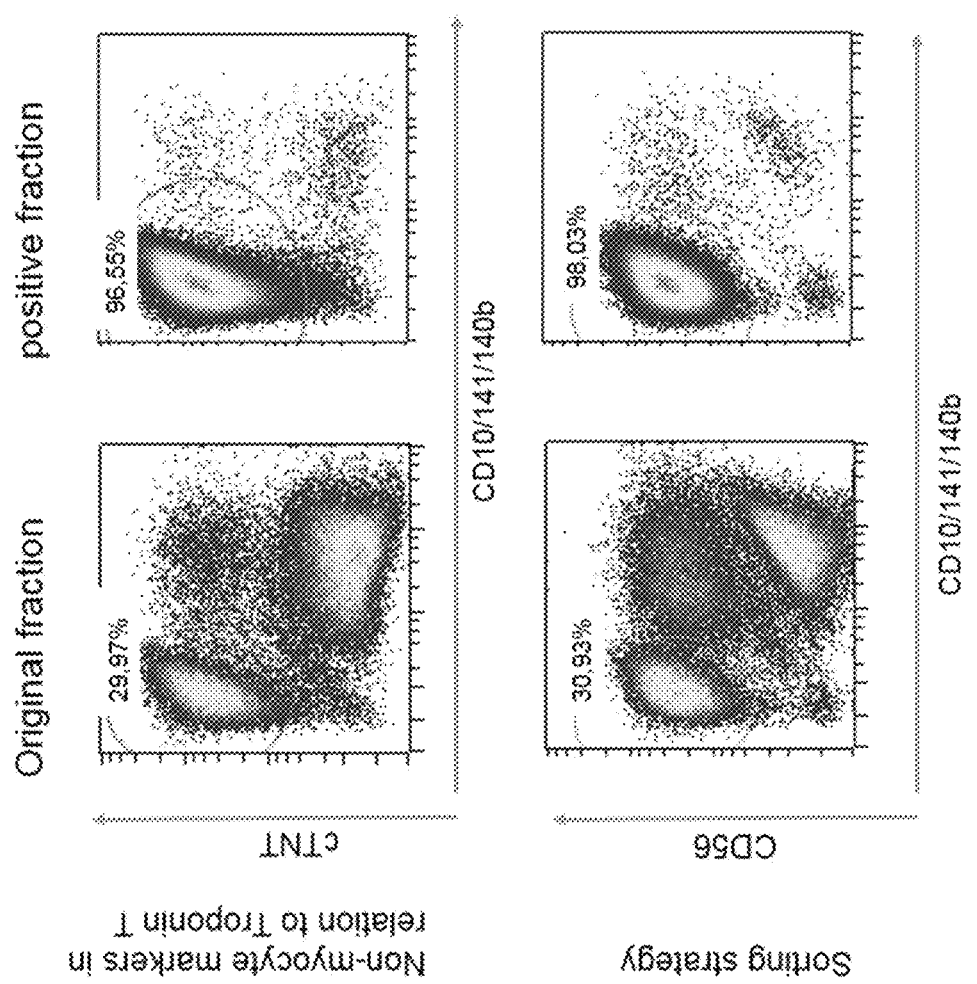
FIG. 9. One example for cardiomyocyte purification by flow cytometry-based cell sorting using the MACSQuant Tyto® (Miltenyi Biotec). To that end the combination of CD10/CD141/CD140b, as non-myocyte markers and CD56, as cardiomyocyte marker, was used. The CD56 single positive cell population was selected for sorting. The dot plots show that cardiomyocytes, i.e. cardiac TroponinT (cTnT) positive cells, are enriched from ca 29% in the original fraction to purities of ca 96% or ca 98% starting from ca 30% cardiac Troponin T (cTnT) positive cells.

Importantly, the above described procedure is applicable to manual magnetic cell separation procedures as well as to automated cell separation procedures using e.g. the autoMACS® Pro or the CliniMACS® Prodigy (both Miltenyi Biotec GmbH) thereby enabling for upscale of the cell separation procedure and directly linking the automated generation of cardiomyocytes with the automated purification of cardiomyocytes in a closed system. Additionally, we found that the same combination of antibodies against surface markers for depletion of non-cardiomyocytes, preferred CD140b, CD141 and CD10, but not limited to this combination, as well as for cardiomyocyte enrichment, preferred but not limited to CD56 can be used for cardiomyocyte enrichment by fluorescence activated cell sorting, using e.g. the MACSQuant Tyto® (Miltenyi Biotec GmbH) (FIG. 9). These data prove that both magnetic and flow cytometry-based cell sorting procedures, using a similar set of antibodies, can be applied to reproducibly purify cardiomyocytes.

Figure 10A:
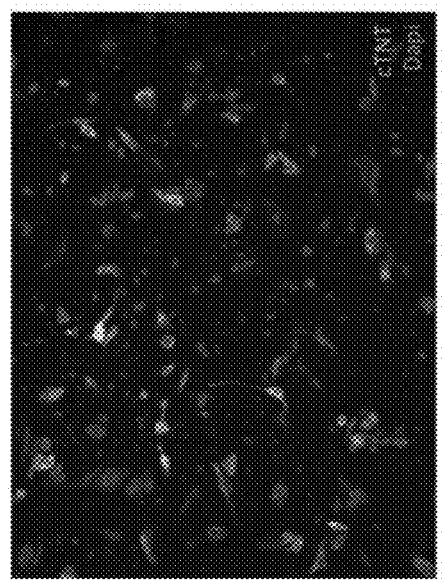
FIGS. 10A-C. Cardiac Troponin T (cTnT) expression was analyzed in the original fraction (FIG. 10A), the cardiomyocyte enriched fraction after removal of non-cardiomyocytes (FIG. 10B) and the cardiomyocyte enriched fraction after removal of non-cardiomyocytes and enrichment of cardiomyocytes (FIG. 10C). Nuclei of cells are labeled with Dapi.
Figure 10B:
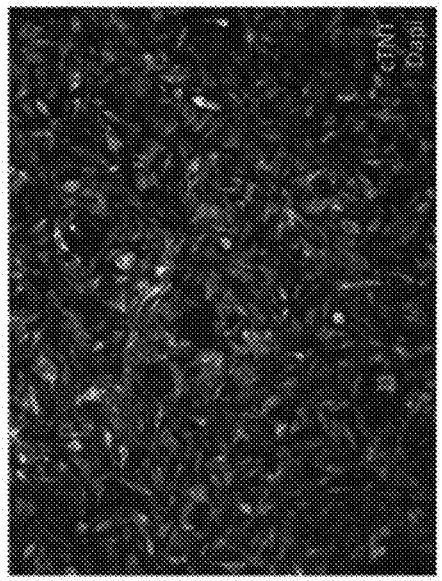
Figure 10C:
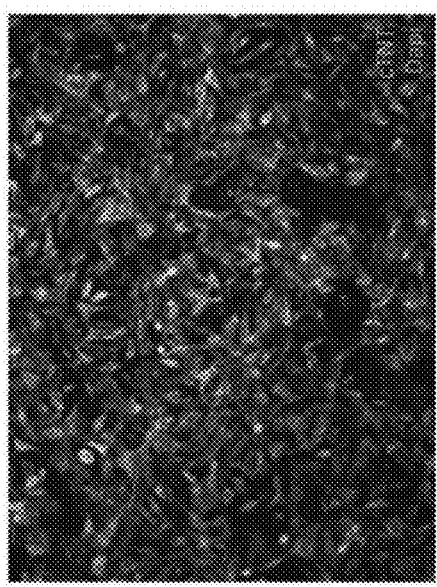
Figure 11B:
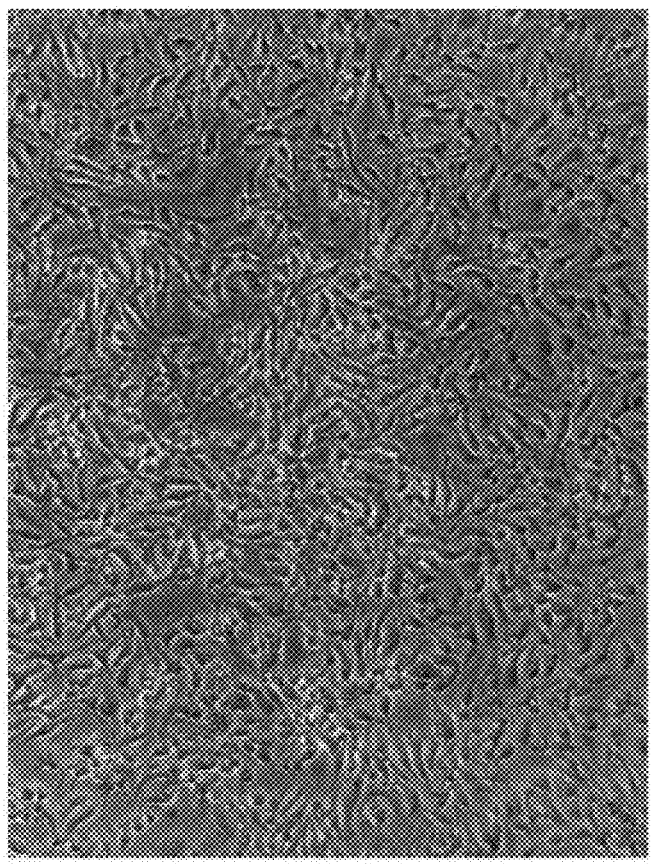
FIGS. 11A-B.
Figure 11A:
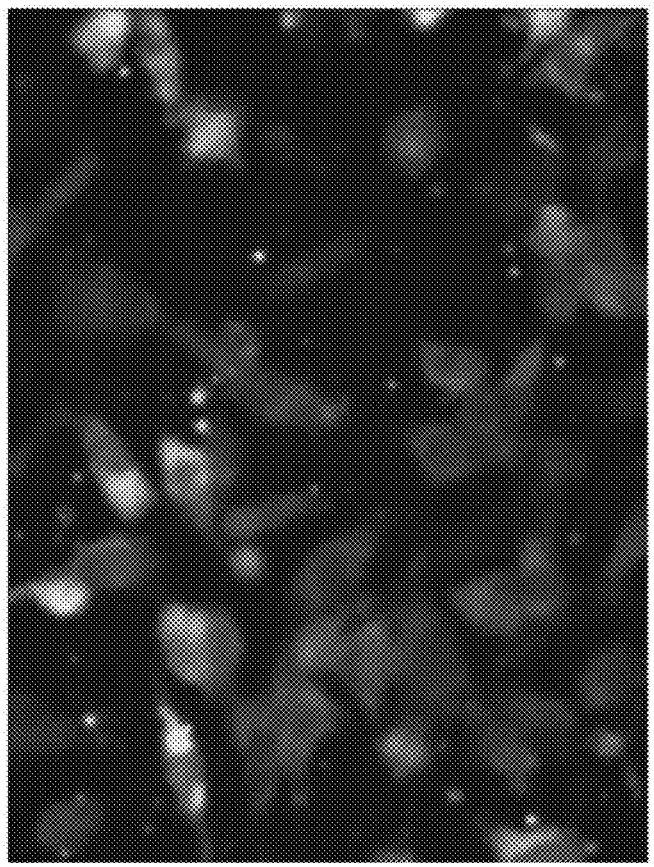

Importantly, regardless of the strategy chosen all separation procedures described herein give rise to highly pure and functional cardiomyocytes: enriched cardiomyocytes plated well, initiated contractions within 24 h after plating and could stably be maintained in culture. Enrichment of cardiomyocytes as well as successful plating after enrichment and sarcomeric structure could additionally be shown by immunofluorescence analysis of Troponin T expression in the original fraction, the cardiomyocyte enriched fraction after depletion and the pure cardiomyocyte population after depletion of non-cardiomyocytes and enrichment for cardiomyocytes (FIGS. 10A-C). Enriched cardiomyocytes showed a typical morphology and labeling with calcium sensitive dyes indicated functionality of purified cardiomyocytes, as typical $Ca^{2+}$ fluxes were observed (FIGS. 11A-B). Additionally, the isolation procedure allows for complete removal of residual pluripotent stem cells, an essential pre-requisite for cell therapies. Further separation of such purified cardiomyocytes into subpopulations is possible using similar cell separation technologies described herein and novel antibodies against cardiomyocyte subpopulation markers as described below.

Figure 12:
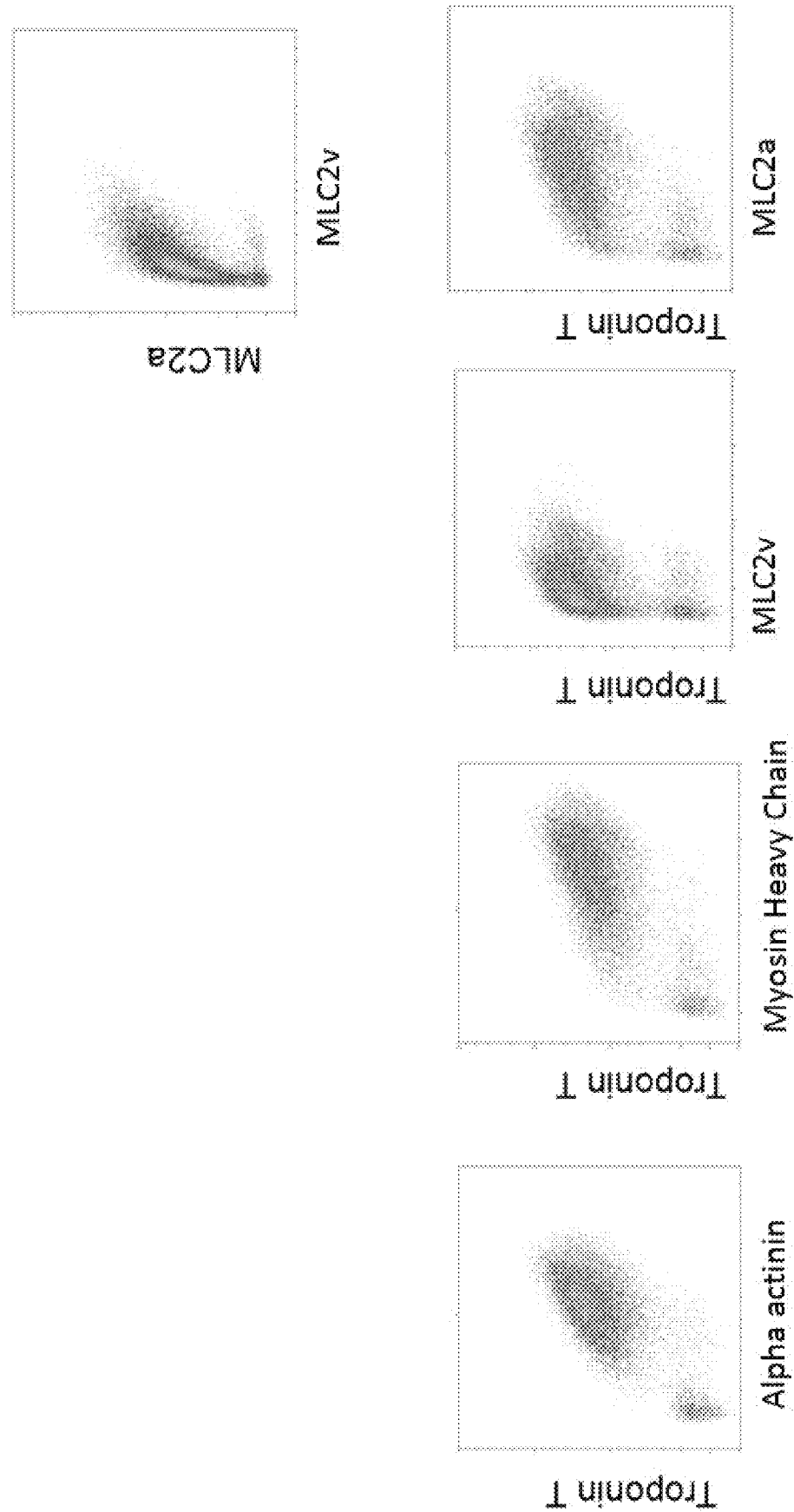
FIG. 12. Flow cytometry analysis of purified cardiomyocytes reveals expression of cardiomyocyte-specific markers, like alpha actinin, myosin heavy chain, and Troponin T, proving the enrichment of true cardiomyocytes. Expression of MLC2a and MLC2v within the Troponin T-positive population indicates the presence of different cardiomyocyte subpopulations.

Flow cytometry analysis of enriched cardiomyocytes indicated expression of cardiomyocyte-specific markers like Myosin Heavy Chain, alpha actinin and Troponin T, proving the enrichment of true cardiomyocytes. Expression of MLC2a ("atrial/immature cardiomyocytes") and MLC2v ("ventricular/mature cardiomyocytes") within the Troponin T positive population indicates presence of different cardiomyocyte subpopulations (FIG. 12). The surface marker screen described above also revealed several surface markers suitable for labeling of PSC-derived cardiomyocyte subpopulations (FIGS. 13A-F), thereby allowing for quantification of CM subpopulations and as well isolation of CM subpopulations.

Cardiomyocytes were detected with a monoclonal antibody against a cardiomyocyte-specific muscle protein (cardiac alpha actinin or Troponin T). Enriched cardiomyocytes or mixtures of cardiomyocytes and non-cardiomyocytes were simultaneously stained with antibodies against human surface epitopes. Surprisingly, flow cytometry analysis revealed that several antibodies detect cardiomyocyte subpopulations although respective antigens have previously not been described for being expressed on hPSC-derived CM subpopulations. Therefore, a further aspect of the invention provides methods for the analysis and isolation of cardiomyocyte subtypes.

Cardiomyocytes derived from a starting cell composition comprising pluripotent and/or multipotent stem cells (step a) of the method as disclosed herein may be labeled with at least one antibody or antigen binding fragment thereof specific for the antigens of a subpopulation of cardiomyocytes, wherein said at least one antibody or fragment thereof is selected from the group consisting of antiPTK7, antiCD81, antiCD276, antiCD239, antiCD298, antiCD49c, antiCD200, antiCD230, antiCD324, antiROR1, antiCD146, antiCD317, antiCD49a, antiCD43, antiCD111, antiCD201, antiCD138, antiCD271, antiCD222, antiCD82, antiCD44, antiCD90, antiCD95, antiCD142, antiNotch-2, antiKIR-2D, antiCD197, antiCD240DCE, antiCD184, antiASCA-1 (GLAST), antiCCR10, antiCDIR, antiCD183, antiCD97, antiCD49b, antiCD134, antiCD13, antifMLP, antiCD83, antiCD79b, antiCD5, antiCD74, and antiCD80.

Said labeling of subpopulations of cardiomyocytes may be performed subsequently after step c) or e) of the method as disclosed herein. Or the depletion of non-cardiomyocytes (step c) and enrichment of subpopulations of cardiomyocytes may be performed simultaneously.

In a preferred embodiment of the invention said at least one antibody or antigen binding fragment thereof specific for the antigens of a subpopulation of cardiomyocytes is exactly one antibody or fragment thereof selected from the group consisting of antiPTK7, antiCD81, antiCD276, antiCD239, antiCD298, antiCD49c, antiCD200, antiCD230, antiCD324, antiROR1, antiCD146, antiCD317, antiCD49a, antiCD43, antiCD111, antiCD201, antiCD138, antiCD271, antiCD222, antiCD82, antiCD44, antiCD90, antiCD95, antiCD142, antiNotch-2, antiKIR-2D, antiCD197, antiCD240DCE, antiCD184, antiASCA-1 (GLAST), antiCCR10, antiCDIR, antiCD183, antiCD97, antiCD49b, antiCD134, antiCD13, antifMLP, antiCD83, antiCD79b, antiCD5, antiCD74, and antiCD80.

The use of one antibody or antigen binding fragment thereof specific for an antigen of a subpopulation of cardiomyocytes selected from said group is sufficient to identify and isolate a cardiomyocyte subpopulation.

Figure 13A:
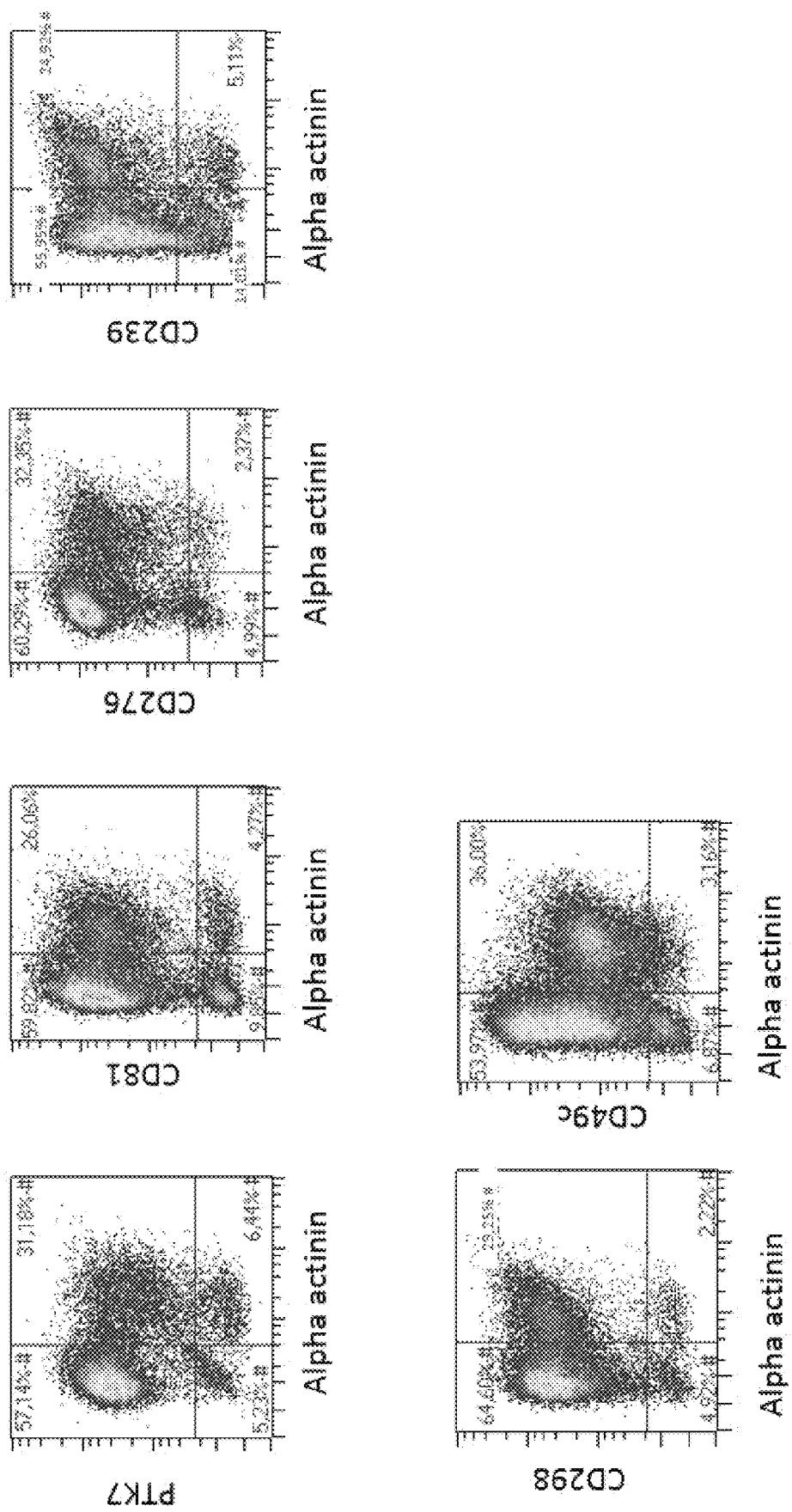
FIGS. 13A-F. Flow cytometry analysis of PSC-derived cardiomyocytes revealed expression of several surface markers within the population of alpha actinin or Troponin T expressing cardiomyocytes. Based on the ratio of co-expression with respective intracellular cardiomyocyte markers (alpha actinin & Troponin T), surface markers were subdivided into 5 groups A: Group 1: 80-95% CMs labeled (FIG. 13A); B: Group 2: 60-80% CMs labeled (FIG. 13B); C: Group 3: 40-60% CMs labeled (FIG. 13C); D: Group 4: 25-40% CMs labeled (FIG. 13D); E and F: Group 5: 10-25% CMs labeled (FIG. 13E and FIG. 13F, respectively)
Figure 13B:
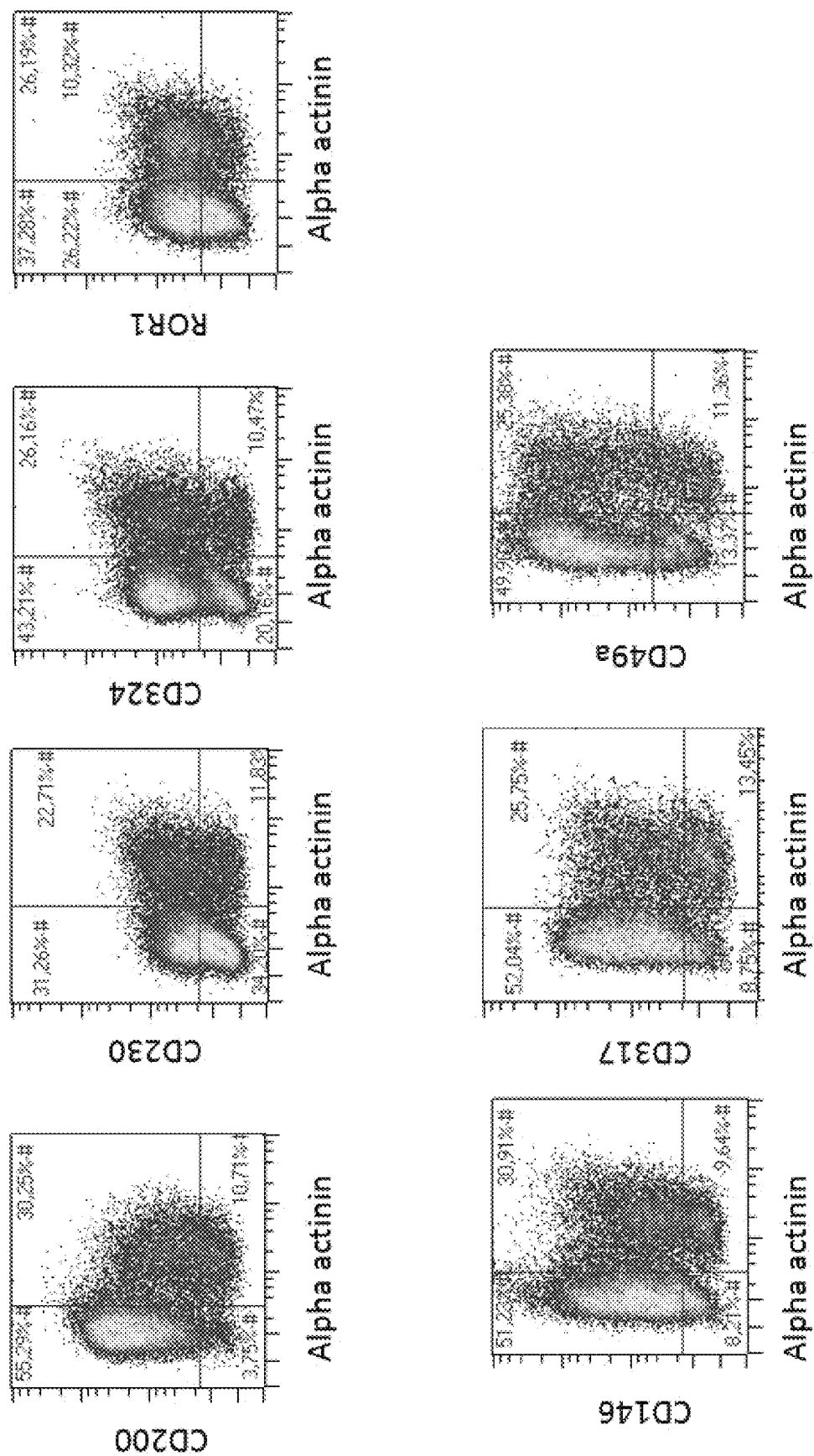
Figure 13C:
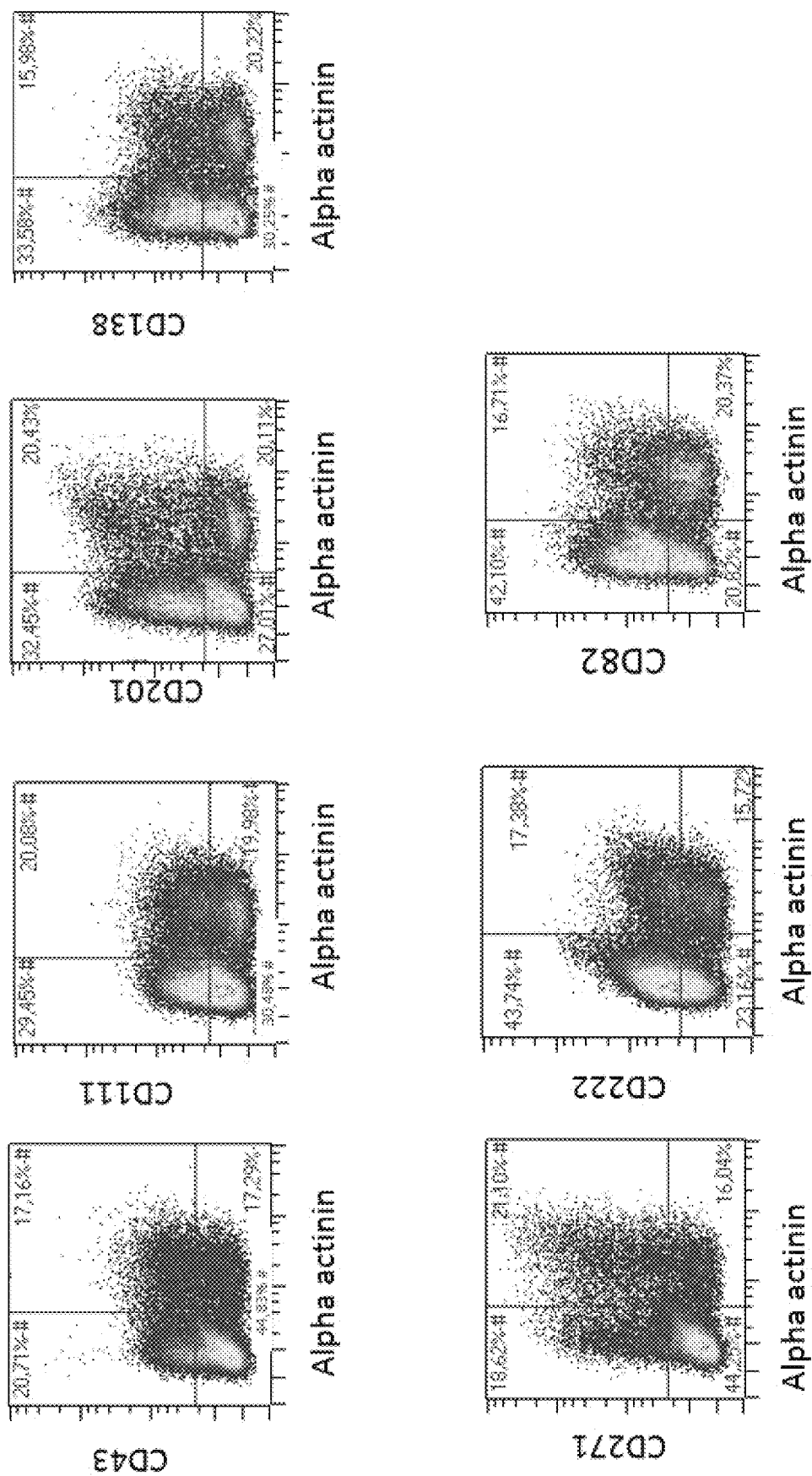
Figure 13D:
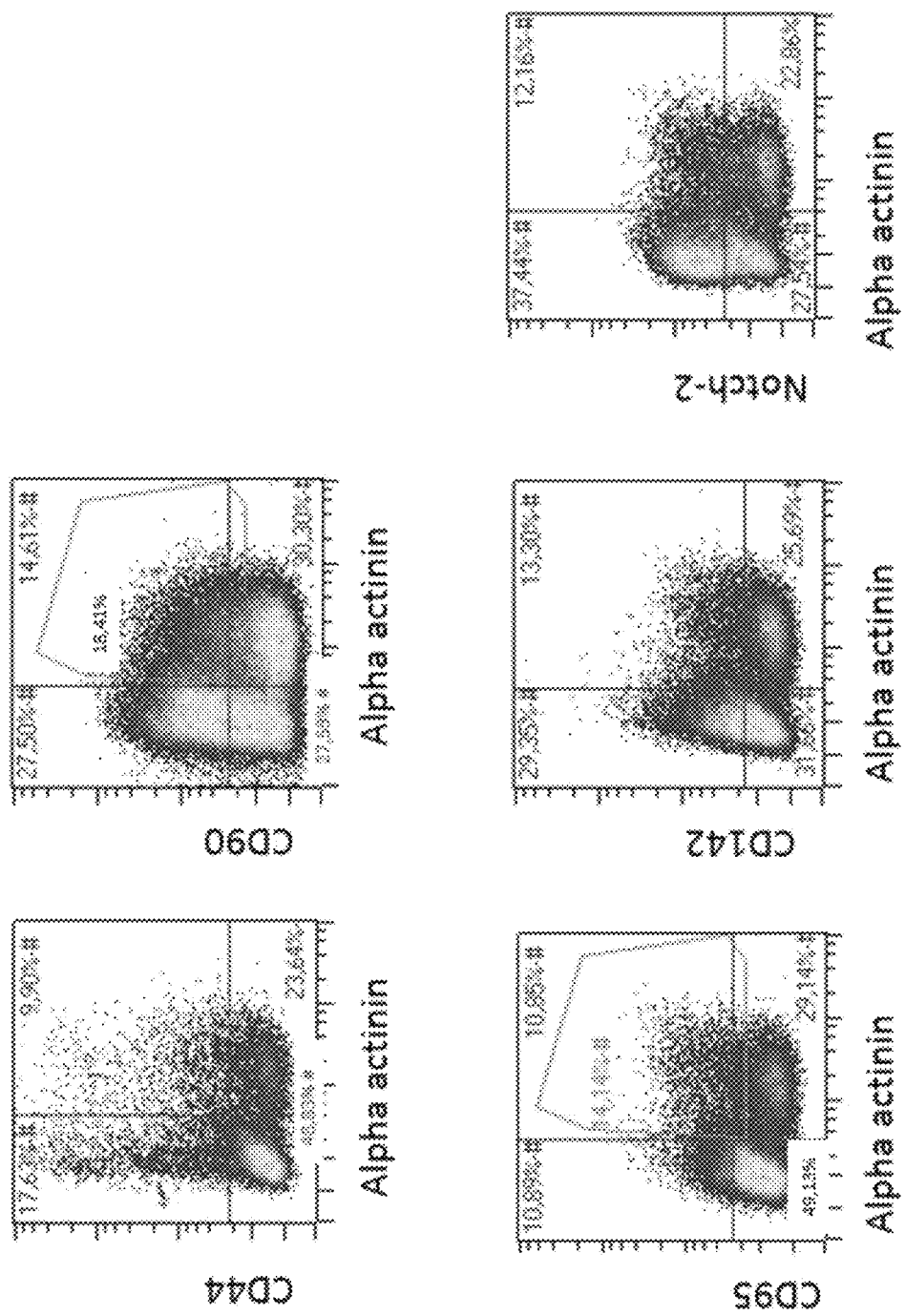
Figure 13E:
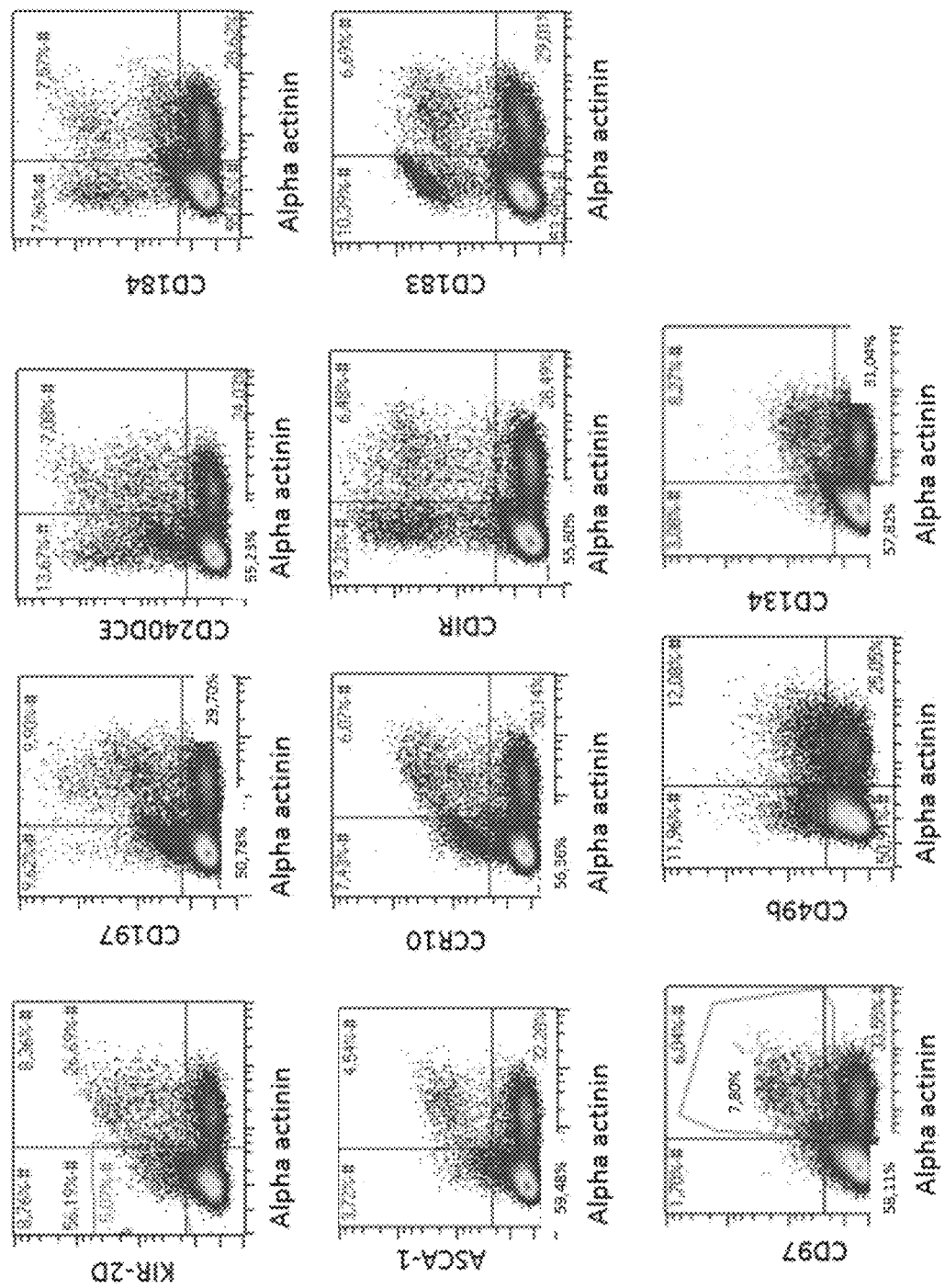
Figure 13F:
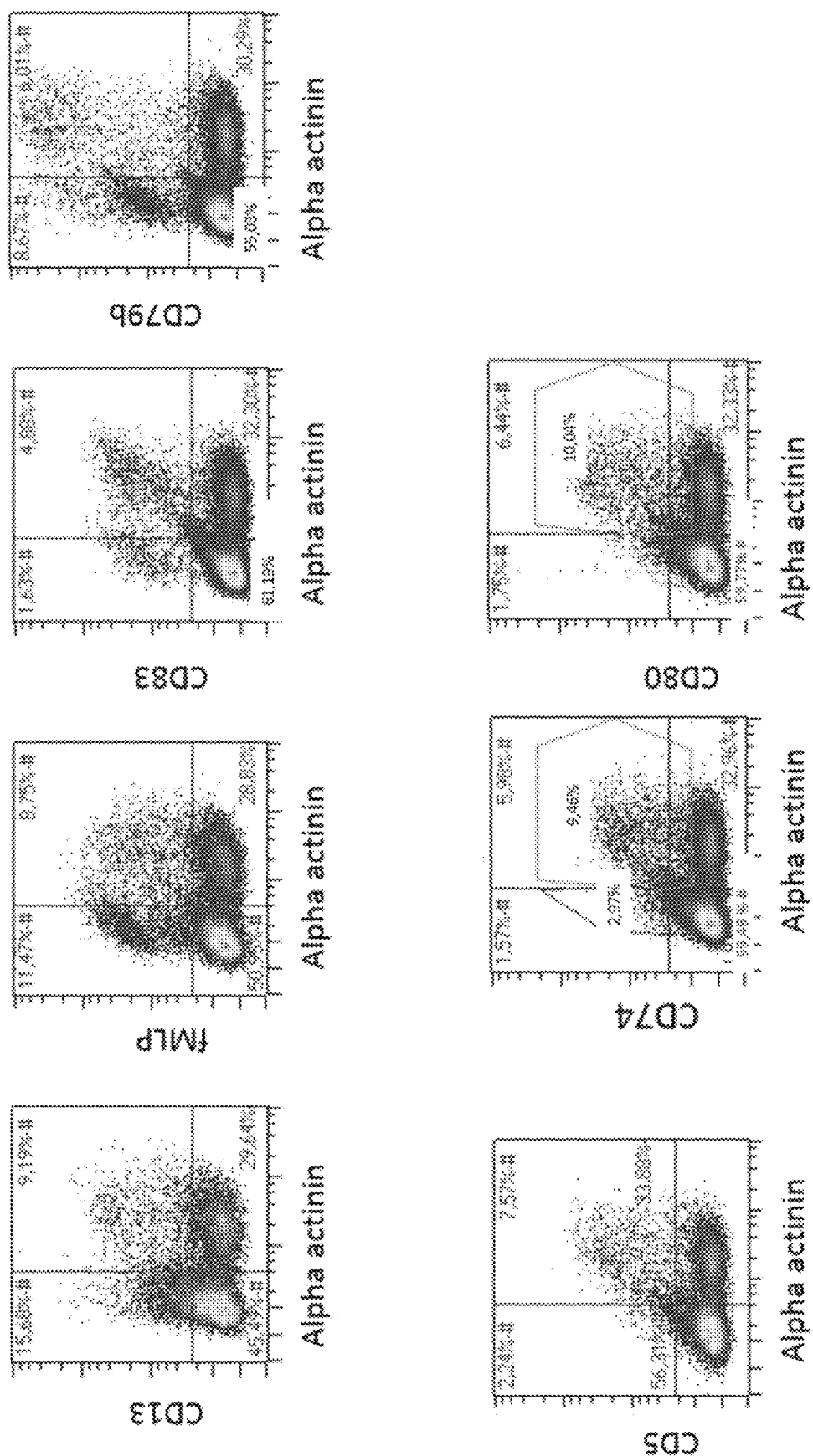
Figure 14A:
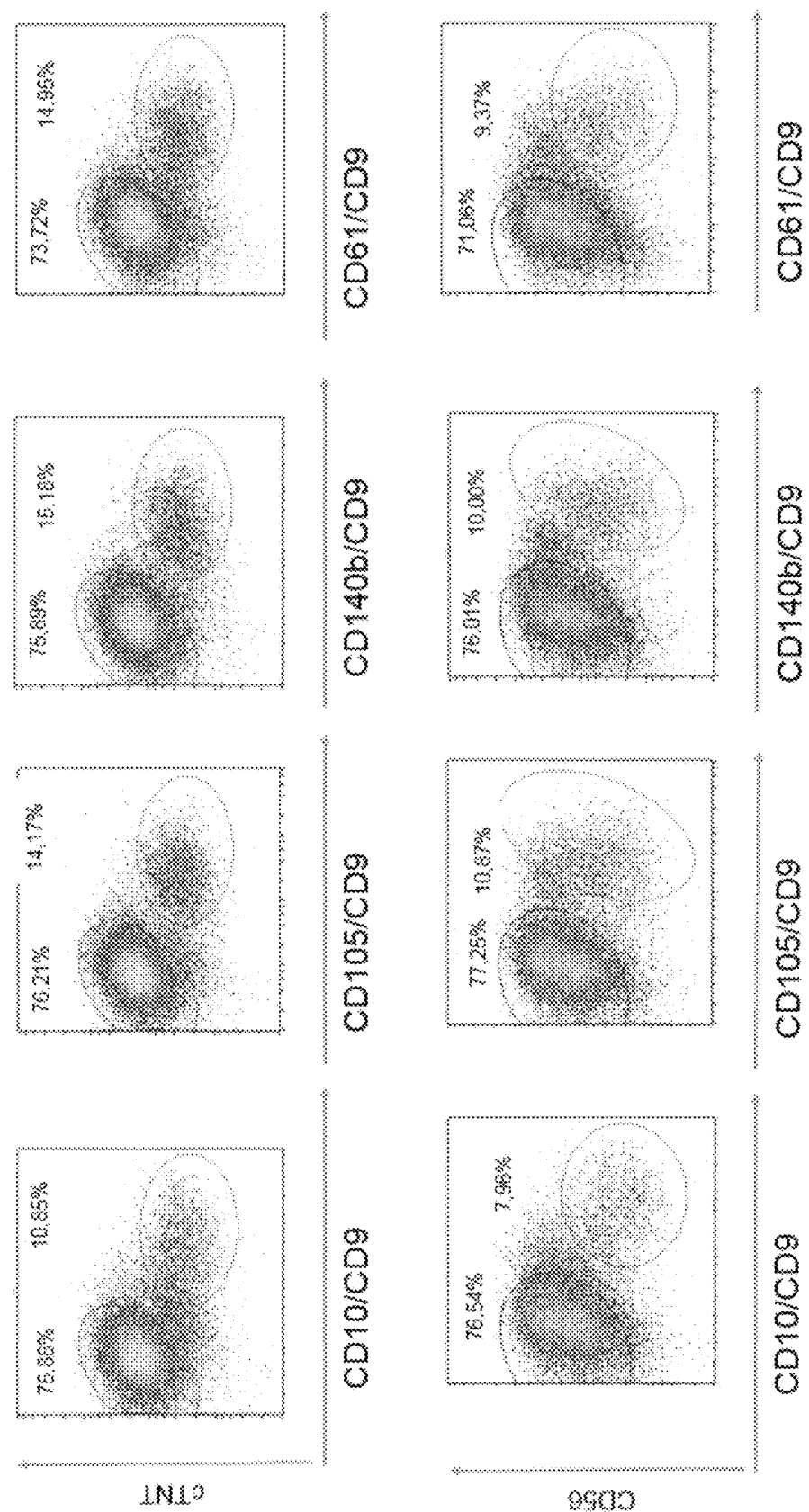
FIGS. 14A-F.
Figure 14B:
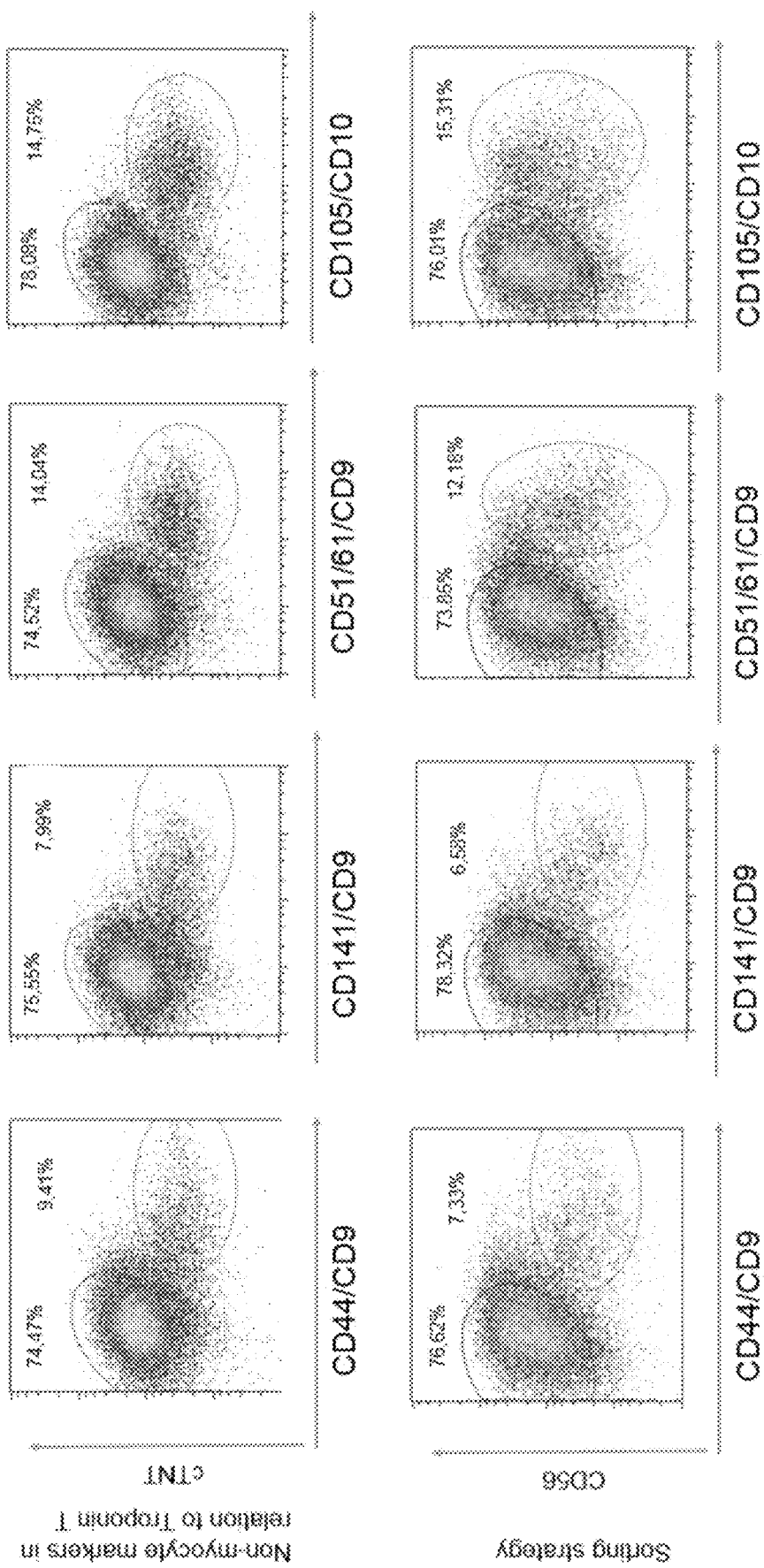
Figure 14C:
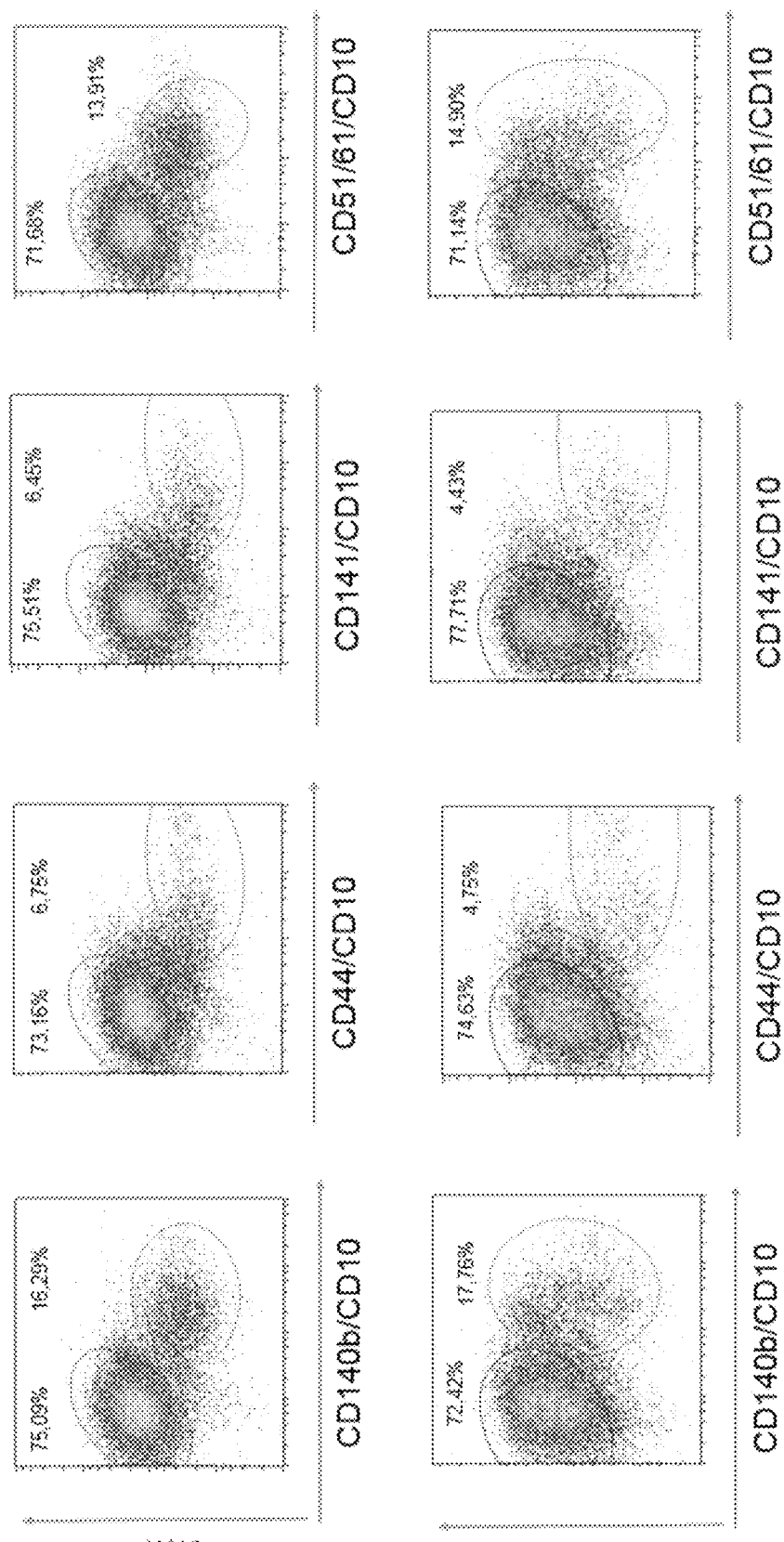
Figure 14D:
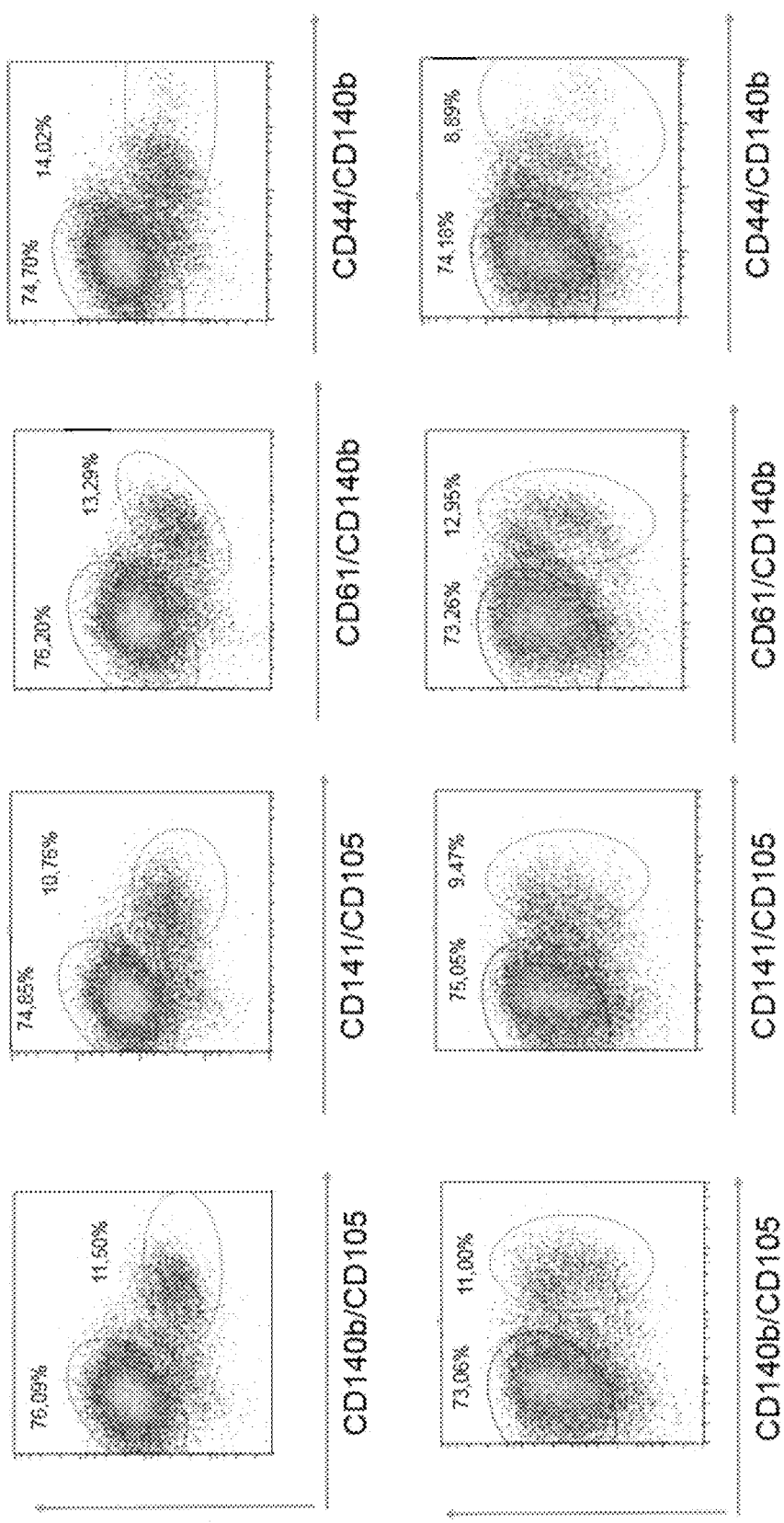
Figure 14E:
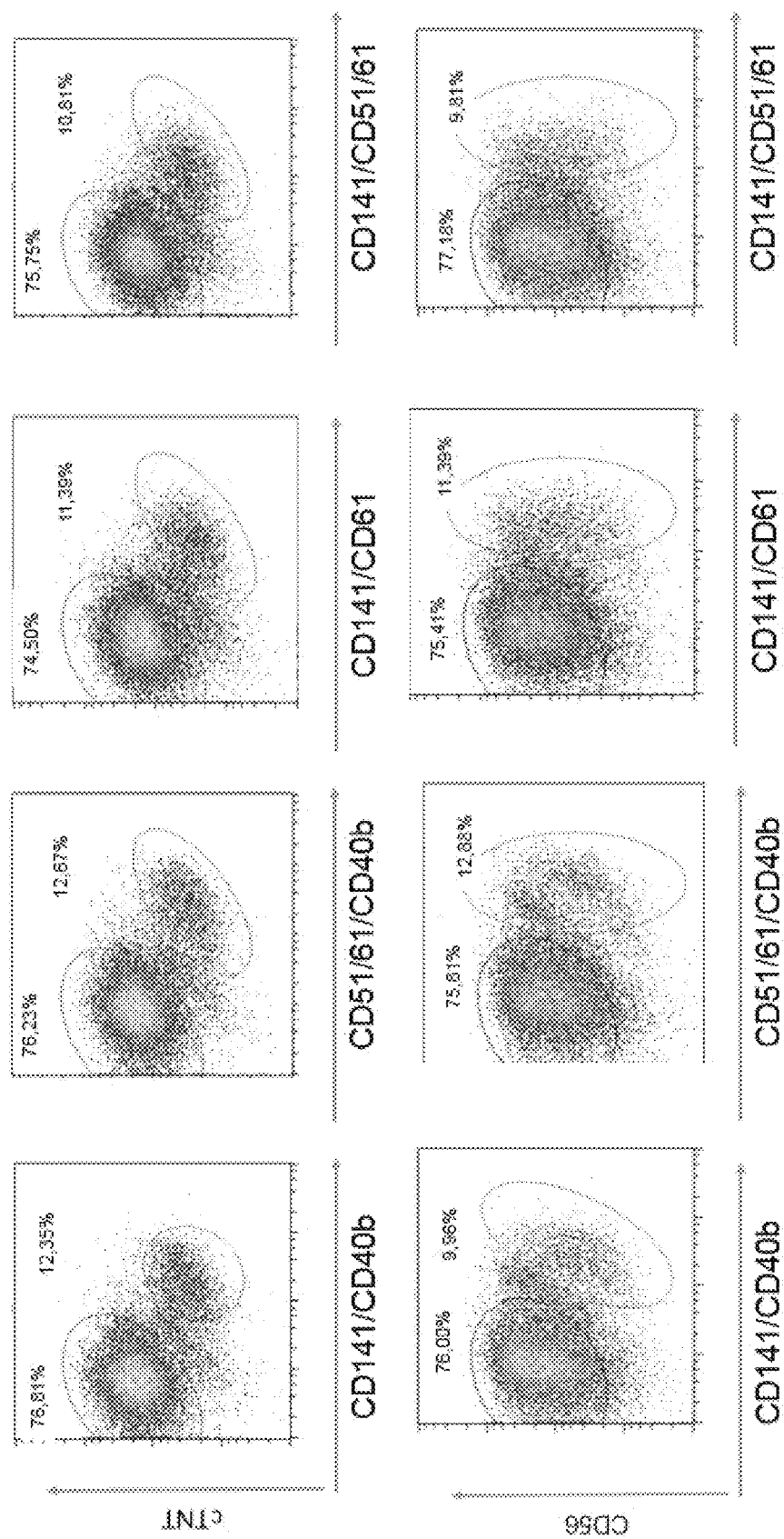
Figure 14F:
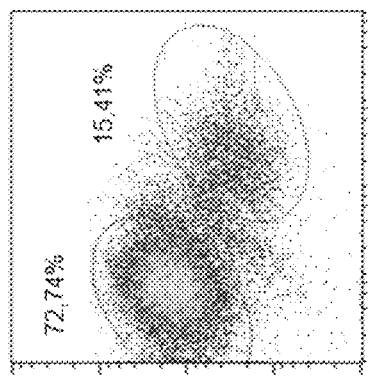
Figure 14F:
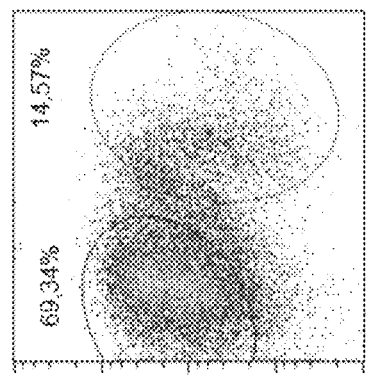
Figure 14F:
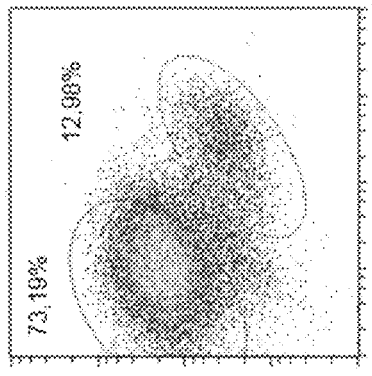
Figure 14F:
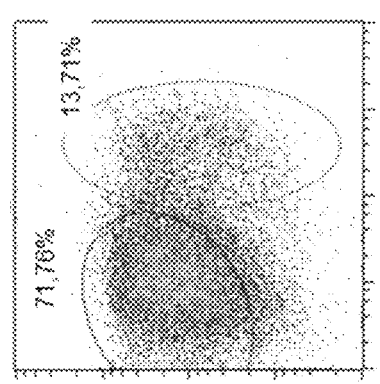

Depending on the co-expression of respective surface markers with intracellular cardiomyocyte markers (alpha actinin or Troponin T) the surface markers were subdivided into various groups (FIGS. 13A-F):

Co-expression of respective surface marker with cardiomyocyte marker (in %):
Group 1, 80-95%: PTK7, CD81, CD276, C239, CD298, CD49c (FIG. 13A)
Group 2, 60-80%: CD200, CD230, CD324, ROR1, CD146, CD317, CD49a (FIG. 13B)
Group 3, 40-60%: CD43, CD111, CD201, CD138, CD271, CD222, CD82 (FIG. 13C)
Group 4, 25-40%: CD44, CD90, CD95, CD142, Notch-2 (FIG. 13D)
Group 5, 10-25%: KIR-2D, CD197, CD240DCE, CD184, ASCA-1 (GLAST), CCR10, CDIR, CD183, CD97, CD49b, CD134, CD13, fMLP, CD83, CD79b, CD5, CD74, CD80 (FIGS. 13E and 13F)

Therefore, all surface markers listed herein can be used to identify, quantify and purify cardiomyocyte subpopulations. Functionality of each subpopulation might outperform the mixture of cardiomyocytes currently used for downstream experiments especially cell replacement therapies. These markers may label cells of different developmental stages or different types of cardiomyocytes and therefore the expression of these markers may play an important role in transplantation as different subpopulations might integrate better into the heart than others. For that reason, these markers are suitable for both quality control and selection of PSC-derived cardiomyocytes and subpopulations generated by cardiomyocyte differentiation protocols known to a person skilled in the art and using similar technologies (magnetic or flow cytometry-based cell separation) for purification of cardiomyocyte subpopulations e.g. for cellular therapies.

In one aspect the present invention provides a method for generation, isolation, detection and/or analysis of cardiomyocytes derived from a starting cell composition comprising pluripotent and/or multipotent stem cells, the method comprising the steps a) Differentiating said pluripotent and/or multipotent stem cells into cardiovascular cells, thereby generating a sample comprising cardiomyocytes and non-cardiomyocytes;

b) Labeling the non-cardiomyocytes of said sample with more than one antibody or antigen binding fragment thereof specific for antigens of non-cardiomyocytes, wherein said more than one antibody or antigen binding fragment fragment thereof is selected from the group consisting of antiCD10, antiCD44, antiCD105, antiCD140b, antiCD61, antiCD141, and antiCD51/61;

c) Depleting said labeled non-cardiomyocytes from said sample.

Said method, wherein said non-cardiomyocytes of said sample are labeled with two, three, four, five, six or seven antibodies or antigen binding fragments thereof specific for antigens of non-cardiomyocytes, wherein said two, three, four, five, six or seven antibodies or antigen binding fragments thereof are selected from the group consisting of antiCD10, antiCD44, antiCD105, antiCD140b, antiCD61, antiCD141, and antiCD51/61;

Said method, wherein said non-cardiomyocytes are labeled with two antibodies or antigen binding fragments thereof, wherein said two antibodies or antigen binding fragments thereof are antiCD10 and antiCD105, antiCD10 and antiCD140b, antiCD10 and antiCD61, antiCD10 and antiCD44, antiCD10 and antiCD141, antiCD10 and antiCD51/61, antiCD105 and antiCD140b, antiCD105 and antiCD61, antiCD105 and antiCD44, antiCD105 and antiCD141, antiCD105 and antiCD51/61, antiCD140b and antiCD61, antiCD140b and antiCD44, antiCD140b and antiCD141, antiCD140b and antiCD51/61, antiCD61 and antiCD44, antiCD61 and antiCD141, antiCD61 and antiCD51/61, antiCD44 and antiCD141, antiCD44 and antiCD51/61, or antiCD141 and antiCD51/61.

Said method, wherein said non-cardiomyocytes are labeled with three antibodies or antigen binding fragments thereof, wherein said antibodies or antigen binding fragments thereof are antiCD140b, antiCD141 and antiCD10.

Said method, wherein said more than one antibody or antigen binding fragment thereof specific for antigens of non-cardiomyocytes are coupled to a tag.

Said depletion may be performed by magnetic cell separation or by fluorescence-activated cell sorting.

Said method wherein the depletion step c) may be performed by magnetic cell separation and said tag may be a magnetic particle or by fluorescence-activated cell sorting and said tag may be a fluorophore.

Said method may comprise the additional steps d) Labeling the cardiomyocytes of said sample with at least one antibody or antigen binding fragment thereof specific for antigen(s) of cardiomyocytes, wherein said at least one antibody or antigen binding fragment thereof is selected from the group consisting of antiPTK7, antiCD99 antiCD276, antiCD56, antiCD59, antiCD147, antiCD239, antiCD298, antiCD49f, antiCD262, antiCD81, antiTra-1-85, antiCD49e, antiCD24, antiCD47, antiCD46, antiCD49c, antiCD51, antiCD29, antiCD98, antiCD63, antiCD146c and antiCD151;

e) Enriching said labeled cardiomyocytes.

Said at least one antibody or antigen binding fragment thereof specific for cardiomyocytes may be antiCD56.

Said method, wherein said at least one antibody or fragment thereof specific for antigen(s) of cardiomyocytes may be coupled to a tag.

Said enriching of labeled cardiomyocytes may be performed by magnetic cell separation or by fluorescence-activated cell sorting.

Said method, wherein the enrichment step e) may be performed by magnetic cell separation and said tag may be a magnetic particle or by fluorescence-activated cell sorting and said tag may be a fluorophore.

Both said depletion and said enriching may be performed by magnetic cell separation, alternatively, both said depletion and said enriching may be performed by fluorescence-activated cell sorting, or further alternatively, said depletion may be performed by magnetic cell separation and said enriching may be performed by fluorescence-activated cell sorting or vice versa.

Said method, wherein the steps may be performed in the order step a), step b), step c), step d) and step e).

Said method comprising steps a) to e), wherein the steps a) to e) may be performed in any order which allows successful isolation or enrichment of said cardiomyocytes.

Said method, wherein said labeling of the cardiomyocytes of said sample with at least one antibody or antigen binding fragment thereof (step d) may be performed after step a) (and before step c)) if said depletion (step c) and said enrichment (step e) are performed simultaneously. Said tags coupled to said more than one antibody or antigen binding fragment thereof specific for antigens of non-cardiomyocytes and said tags coupled to said at least one antibody or antigen binding fragment thereof specific for antigen(s) of cardiomyocytes may be distinguishable (or distinct) tags if said depletion (step c) and said enrichment (step e) are performed simultaneously. Distinguishable tags may be e.g. FITC and APC if the tags are fluorophores or may be e.g. MACSiBeads™ (Miltenyi Biotec GmbH) and MicroBeads® (Miltenyi Biotec GmbH) if the tags are magnetic particles.

Said method, wherein the magnetic particle coupled to said more than one antibody or antigen binding fragment thereof specific for antigen(s) of non-cardiomyocytes and the magnetic particle coupled to said at least one antibody or fragment thereof specific for antigen(s) of cardiomyocytes are distinguishable magnetic particles if the labeling of the non-cardiomyocytes (step b) and the labeling of the cardiomyocytes (step d) is performed simultaneously or wherein the fluorophore coupled to said more than one antibody or antigen binding fragment thereof specific for antigen(s) of non-cardiomyocytes and the fluorophore coupled to said at least one antibody or fragment thereof specific for antigen(s)

of cardiomyocytes are distinguishable fluorophores if the labeling of the non-cardiomyocytes (step b) and the labeling of the cardiomyocytes (step d) is performed simultaneously.

Alternatively, said tag or tags may be other molecules than magnetic particles or fluorophores, e.g. haptens like biotin, which allow for indirect immobilization of the antibodies used the method disclosed herein.

At least steps c) and e) may be performed simultaneously by fluorescence-activated cell sorting if said tags are distinguishable fluorophores. Alternatively all steps may be performed subsequently.

Said method comprising steps a) to c), wherein the method comprises after step c) the additional steps:
- I) Labeling the cardiomyocytes of step c) with at least one antibody or antigen binding fragment thereof specific for the antigens of a subpopulation of cardiomyocytes, wherein said at least one antibody or antigen binding fragment thereof is selected from the group consisting of antiPTK7, antiCD81, antiCD276, antiCD239, antiCD298, antiCD49c, antiCD200, antiCD230, antiCD324, antiROR1, antiCD146, antiCD317, antiCD49a, antiCD43, antiCD111, antiCD201, antiCD138, antiCD271, antiCD222, antiCD82, antiCD44, antiCD90, antiCD95, antiCD142, anti-Notch-2, antiKTR-2D, antiCD197, antiCD240DCE, antiCD184, antiASCA-1 (GLAST), antiCCR10, antiCDIR, antiCD183, antiCD97, antiCD49b, antiCD134, antiCD13, antifMLP, antiCD83, antiCD79b, antiCD5, antiCD74, and antiCD80
- II) Enriching said labeled cardiomyocytes of step I), thereby enriching a subpopulation of cardiomyocytes.

Said method comprising steps a) to e), wherein the method after step e) comprises the additional steps:
- I) Labeling the cardiomyocytes of step e) with at least one antibody or antigen binding fragment thereof specific for the antigens of subpopulation of cardiomyocytes, wherein said at least one antibody or antigen binding fragment thereof is selected from the group consisting of antiPTK7, antiCD81, antiCD276, antiCD239, antiCD298, antiCD49c, antiCD200, antiCD230, antiCD324, antiROR1, antiCD146, antiCD317, antiCD49a, antiCD43, antiCD111, antiCD201, antiCD138, antiCD271, antiCD222, antiCD82, antiCD44, antiCD90, antiCD95, antiCD142, anti-Notch-2, antiKTR-2D, antiCD197, antiCD240DCE, antiCD184, antiASCA-1 (GLAST), antiCCR10, antiCDIR, antiCD183, antiCD97, antiCD49b, antiCD134, antiCD13, antifMLP, antiCD83, antiCD79b, antiCD5, antiCD74, and antiCD80
- II) Enriching said labeled cardiomyocytes of step I), thereby enriching a subpopulation of cardiomyocytes.

Generally, the differentiation step of said method may be performed with any medium suitable to differentiate said pluripotent and/or multipotent stem cells into cardiomyocytes (step a) of the method as disclosed herein). The differentiation of pluripotent/multipotent stem cells into cardiomyocytes as well as the purification of cardiomyocytes and cardiomyocyte subtypes may be performed in an automated manner in a closed system. A preferred closed system used for the differentiation of pluripotent/multipotent stem cells into cardiomyocytes may be the CliniMACS® prodigy from Miltenyi Biotec.

In another aspect the invention provides a substantially pure composition of cardiomyocytes wherein said cardiomyocytes are obtained by the method as described above and disclosed herein.

In a further aspect the invention provides a pharmaceutical composition comprising a composition of cardiomyocytes, wherein said cardiomyocytes are obtained by the method as described above and disclosed herein.

In a further aspect the invention provides a substantially pure composition of a subpopulation of cardiomyocytes, wherein said subpopulation comprises the expression of at least one surface marker (antigen) selected from the group of surface markers consisting of PTK7, CD81, CD276, CD239, CD298, CD49c, CD200, CD230, CD324, ROR1, CD146, CD317, CD49a, CD43, CD111, CD201, CD138, CD271, CD222, CD82, CD44, CD90, CD95, CD142, Notch-2, KIR-2D, CD197, CD240DCE, CD184, ASCA-1 (GLAST), CCR10, CDIR, CD183, CD97, CD49b, CD134, CD13, fMLP, CD83, CD79b, CD5, CD74, and CD80 wherein said composition is obtained by a method for enrichment of cardiomyocytes derived from a starting cell composition comprising pluripotent and/or multipotent stem cells, the method comprising the steps
- a) Differentiating said human pluripotent and/or multipotent stem cells into cardiovascular cells, thereby generating a sample comprising cardiomyocytes and non-cardiomyocytes;
- b) Labeling the non-cardiomyocytes of said sample with more than one antibody or fragment thereof specific for antigen(s) of non-cardiomyocytes, wherein said more than one antibody or fragment thereof is selected from the group consisting of antiCD10, antiCD44, antiCD105, antiCD140b, antiCD61, antiCD141, antiCD171, and antiCD51/61;
- c) Depleting said labeled non-cardiomyocytes from said sample,
- d) Labeling the cardiomyocyte of step c) with at least one antibody or fragment thereof specific for the antigen of said subpopulation of cardiomyocytes, wherein said at least one antibody or fragment thereof is selected from the group consisting of antiPTK7, antiCD81, antiCD276, antiCD239, antiCD298, antiCD49c, antiCD200, antiCD230, antiCD324, antiROR1, antiCD146, antiCD317, antiCD49a, antiCD43, antiCD111, antiCD201, antiCD138, antiCD271, antiCD222, antiCD82, antiCD44, antiCD90, antiCD95, antiCD142, antiNotch-2, antiKIR-2D, antiCD197, antiCD240DCE, antiCD184, antiASCA-1 (GLAST), antiCCR10, antiCDIR, antiCD183, antiCD97, antiCD49b, antiCD134, antiCD13, antifMLP, antiCD83, antiCD79b, antiCD5, antiCD74, and antiCD80.
- e) Enriching said labeled cardiomyocyte of step d), thereby generating a composition of a subpopulation of cardiomyocytes.

Said subpopulation of cardiomyocytes may be for pharmaceutical use.

In another aspect the invention provides a substantially pure composition of a subpopulation of cardiomyocytes, wherein said subpopulation comprises the expression of at least one surface marker (antigen) selected from the group consisting of PTK7, CD81, CD276, CD239, CD298, CD49c, CD200, CD230, CD324, ROR1, CD146, CD317, CD49a, CD43, CD111, CD201, CD138, CD271, CD222, CD82, CD44, CD90, CD95, CD142, Notch-2, KIR-2D, CD197, CD240DCE, CD184, ASCA-1 (GLAST), CCR10, CDIR, CD183, CD97, CD49b, CD134, CD13, fMLP, CD83, CD79b, CD5, CD74, and CD80, wherein said composition is obtained by a method for generation and isolation of cardiomyocytes derived from a starting cell composition comprising pluripotent and/or multipotent stem cells, the method comprising the steps
- a) Differentiating said pluripotent and/or multipotent stem cells into cardiovascular cells, thereby generating a sample comprising cardiomyocytes and non-cardiomyocytes;
- b) Labeling the non-cardiomyocytes of said sample with more than one antibody or antigen binding fragment thereof specific for antigen(s) of non-cardiomyocytes, wherein said at least one antibody or fragment thereof is selected from the group consisting of antiCD10, antiCD44, antiCD105, antiCD140b, antiCD61, antiCD141, antiCD171, and antiCD51/61;
- c) Depleting said labeled non-cardiomyocytes from said sample,
- d) Labeling the cardiomyocytes of said sample with at least one antibody or fragment thereof specific for antigen(s) of cardiomyocytes, wherein said at least one antibody or fragment thereof is selected from the group consisting of antiPTK7, antiCD99, antiCD276, antiCD56, antiCD59, antiCD147, antiCD239, antiCD298, antiCD81, antiCD49f, antiCD262, antiCD281, antiTra-1-85, antiCD49e, antiCD24, antiCD47, antiCD46, antiCD49c, antiCD51, antiCD29, antiCD98, antiCD63, antiCD146c and antiCD151;
- e) Enriching said labeled cardiomyocytes
- f) Labeling the cardiomyocytes of step e) with at least one antibody or fragment thereof specific for the antigens of said subpopulation of cardiomyocytes, wherein said at least one antibody or fragment thereof is selected from the group consisting of antiPTK7, antiCD81, antiCD276, antiC239, antiCD298, antiCD49c, antiCD200, antiCD230, antiCD324, antiROR1, antiCD146, antiCD317, antiCD49a, antiCD43, antiCD111, antiCD201, antiCD138, antiCD271, antiCD222, antiCD82, antiCD44, antiCD90, antiCD95, antiCD142, antiNotch-2, antiKTR-2D, antiCD197, antiCD240DCE, antiCD184, antiASCA-1 (GLAST), antiCCR10, antiCDIR, antiCD183, antiCD97, antiCD49b, anti134, antiCD13, antifMLP, antiCD83, antiCD79b, antiCD5, antiCD74, and antiCD80
- g) Enriching said labeled cardiomyocytes of step 0, thereby generating a composition of a subpopulation of cardiomyocytes.

Embodiments

Method for purification of PSC-derived cardiomyocytes exemplified by magnetic cell separation using MACS® cell separation technology (Miltenyi Biotec GmbH):

The starting point for the isolation of PSC derived cardiomyocytes is a mixed cell population of PSC derived cardiomyocytes and non-cardiomyocytes, that is typically obtained from cardiovascular differentiations of human PSCs. The differentiation process may be performed as shown in FIGS. 1A-C.

The magnetic isolation of human pluripotent stem cell (PSC)-derived cardiomyocytes is performed in a one or two-step procedure. First, the non-cardiomyocytes are magnetically labeled with a combination of antibodies (more than one antibody) against non-cardiomyocyte markers (e.g. CD140b, CD141, CD10) and subsequently depleted by separation over a MACS® Column (Miltenyi Biotec GmbH), which is placed in the magnetic field of a MACS® Separator (Miltenyi Biotec GmbH).

In the second step, the PSC-derived cardiomyocytes are magnetically labeled with at least one antibody against cardiomyocyte markers (e.g. CD56) and isolated by positive selection from the pre-enriched PSC-derived cardiomyocyte fraction by separation over a MACS® Column (Miltenyi Biotec), which is placed in the magnetic field of a MACS® Separator (Miltenyi Biotec).

After removing the column from the magnetic field, the magnetically retained PSC-derived cardiomyocytes can be eluted as the positively selected cell fraction. Magnetic CM (Cardiomyocyte) enrichment can also be performed in an automated manner using e.g. the autoMACS® Pro (Miltenyi Biotec GmbH) as well as a closed system such as the CliniMACS® Prodigy (Miltenyi Biotec GmbH).

Other magnetic cell separation systems than the MACS® technology may also be used. It is not intended to restrict the magnetic cell separation process to the MACS® technology which is used herein as an example only.

Method for purification of PSC-derived cardiomyocytes exemplified by fluorescence-activated cell sorting technology using MACS® Quant Tyto (Miltenyi Biotec GmbH):

For fluorescence activated cell sorting (FACS) a one or two step sorting procedure is possible. PSC-derived cardiomyocytes and non-cardiomyocytes are labeled with a combination of antibodies against non-cardiomyocyte markers (e.g. CD140b, CD141, CD10) and antibodies against a cardiomyocyte surface marker (e.g. CD56) using different fluorophores. Cardiomyocytes positive for the cardiomyocyte surface marker and negative for the non-cardiomyocyte markers can then be sorted using a flow cytometer e.g. the MACS® Quant Tyto (Miltenyi Biotec GmbH), which enables also cell sorting in a closed, sterile system.

Purified cardiomyocytes plate efficiently, independent of the separation strategy chosen and start to contact after replating in culture.

Other fluorescence-activated cell sorting system than the MACS® Quant Tyto (Miltenyi Biotec GmbH) may also be used. It is not intended to restrict the magnetic cell separation process to the MACS® Quant Tyto which is used herein as an example only.

Method for purification of PSC-derived cardiomyocytes in a closed system:

Herein it is also disclosed that the methods of the present invention can be performed in a closed preferentially automated system resulting in enriched cardiomyocytes generated under GMP or GMP-like conditions. Unexpectedly, it was found that the method of the present invention is accessible to an automated process using said closed system.

The cells of the composition obtained by the methods of the present invention may, for example, be used in cell replacement therapies for patients as a therapeutic treatment to ameliorate or reverse symptoms caused by the loss of cardiomyocytes in a patient suffering from heart diseases accompanied by loss of cardiomyocytes, like coronary heart disease.

In one embodiment of the invention said method is an automated method (process). The method comprises (1) the generation of PSC-derived cardiomyocytes as well as (2) the purification of cardiomyocytes and cardiomyocyte subpopulations in a closed system.

Transfer of cardiovascular differentiation protocols to a closed system require the stable performance and scalability of respective differentiations. Standardization of a cardiomyocyte purification protocol requires efficient coverage of variations in differentiation efficiencies and surface marker expression. Therefore, the robust performance of for example the antibody cocktail antiCD140b, antiCD141 and antiCD10 for the removal of non-cardiomyocytes as well as for example antiCD56 antibodies for further enrichment of cardiomyocytes independent of the differentiation protocol or the stem cell line used or the time point of differentiation ensures a standardized process in closed systems. Other previously described antibody combinations against non-cardiomyocyte markers like antiCD49a, antiCD90 and antiCD31 (FIG. 4) are not restricted to non-cardiomyocytes or label only subpopulations of non-cardiomyocytes when used alone (antiCD140b, FIG. 5) and are therefore unsuitable for the use in a closed, automated system ensuring high purification of cardiomyocytes. Additionally, enrichment of cardiomyocytes by only antibodies against CD56 are insufficient as CD56 is known to be expressed on non-cardiomyocytes as well and therefore requiring the removal of CD56-positive non-cardiomyocytes in a first step. Therefore, antibody combinations disclosed herein are suitable for a closed, automated cardiomyocyte generation and purification procedures. Additionally, selective enrichment of cardiomyocyte subpopulations from cardiomyocytes delivered by methods disclosed herein allow for further refinement of the cardiomyocyte population in a closed system.

Therefore, all steps resulting in a better defined cell composition, free of contaminating pluripotent cells or non-cardiomyocytes, help to increase safety and efficacy of a clinical application of the cell composition such as a potential cell product for treatment of cardiovascular diseases.

Such a closed system may be able to perform most, preferentially all steps in an automated manner. Exemplarily the CliniMACS Prodigy® (Miltenyi Biotec GmbH, Germany) is used herein as a closed cell sample processing system on which an automated process was implemented. This system is disclosed in WO2009/072003 in detail. But it is not intended to restrict the use of the method of the present invention to the CliniMACS Prodigy (Miltenyi Biotec GmbH, Germany).

Definitions

Unless defined otherwise, technical and scientific terms used herein have the same meaning as commonly understood by one of ordinary skill in the art to which this invention belongs.

The term "pluripotent stem cell" (PSC) as used herein refers to cells being capable to self renew and have the potential to differentiate into any of the embryonic germ layers endoderm, mesoderm and ectoderm and cells derived from this. These criteria hold true for embryonic stem cells (ESC) and induced pluripotent stem cells (iPSC). Preferentially these cells are human. Human embryonic stem cells can be isolated from embryos without destruction as disclosed e.g. in WO 03/046141. Different degrees of pluripotency are known in the art, referred to as "primed state" pluripotent stem cells, "naive state" pluripotent stem cells or "reset stage" pluripotent stem cells.

The term "induced pluripotent stem cells (iPSC)" as used herein refers to pluripotent cells generated by conversion of cells of lower potency, i.e. more differentiated cells, typically a somatic cell, to a state of pluripotency, the resulting cells being capable to self renew and having the potential to differentiate into any of the embryonic germ layers endoderm, mesoderm and ectoderm and cells derived from this.

The term "multipotent stem cell" as used herein refers to progenitor cells that have the capacity to differentiate into multiple but limited cell types.

The term "differentiation" as used herein refers to cellular differentiation, a term used in developmental biology, and describes the process by which a less specialized cell becomes a more specialized cell type. In vitro, differentiation of stem cells can occur spontaneously or is induced intentionally by adding differentiation inducing agents such as specialized cultivation media, cytokines, receptor antagonists or small molecules to the cultivation media. "Day 0" indicates the starting day of differentiation. The differentiation process may last as long as desired by the operator and can be performed as long as the cell culture medium has conditions, which allow the cells to survive and/or grow and/or proliferate.

The term "starting cell composition" as used herein refers to a sample comprising pluripotent and/or multipotent stem cells and other cells in any ratio or a mixture of said pluripotent or multipotent stem cells to the other cells in that sample. Preferentially, said starting cell composition comprises cells that are to 50%, 60%, 70%, 80%, 90%, 95, 99% or 100% pluripotent or multipotent stem cells. Preferentially the starting cell composition consists of pluripotent and/or multipotent stem cells. Said other cells may be spontaneously differentiated cells originating from said pluripotent or multipotent stem cells. Said spontaneously differentiated cells are characterized by loss of expression of stem cell associated markers and initiation of expression of differentiation associated markers. Preferentially, the cells are viable. The cells originate from humans.

The term "robust performance" or "robustness" as used herein refers to the purification of cardiomyocytes to purities of up to 98% independent of variations in antigen expression, differentiation efficiencies, stem cell clones used and time points of differentiations selected for cardiomyocyte enrichment. The purification method is based either on a 1- or 2-step cell separation procedure as disclosed herein with combinations of antibodies for labeling non-cardiomyocytes or cardiomyocytes as disclosed herein allowing the implementation of an automated process for generation and separation of the cells expressing said antigens.

The terms "specifically binds to" or "specific for" with respect to an antigen-binding molecule, e.g. an antibody or antigen binding fragment thereof, refer to an antigen-binding molecule (in case of an antibody or antigen binding fragment thereof to an antigen-binding domain) which recognizes and binds to a specific antigen in a sample, e.g. CD140b, CD141, CD10, CD56, but does not substantially recognize or bind other antigens in said sample. An antigen-binding domain of an antibody or fragment thereof that binds specifically to an antigen from one species may bind also to that antigen from another species. This cross-species reactivity is not contrary to the definition of "specific for" as used herein. An antigen-binding domain of an antibody or fragment thereof that specifically binds to an antigen, e.g. the CD140b, CD141, CD10, CD56 antigens, may also bind substantially to different variants of said antigen (allelic variants, splice variants, isoforms etc.). This cross reactivity is not contrary to the definition of that antigen-binding domain as specific for the antigen, e.g. for CD140b, CD141, CD10, CD56.

The term "closed system" as used herein refers to any closed system which reduces the risk of cell culture contamination while performing culturing processes such as the introduction of new material and performing cell culturing steps such as proliferation, differentiation, activation, and/or separation of cells. Such a system allows to operate under GMP or GMP-like conditions ("sterile") resulting in cell compositions which are clinically applicable. Herein exemplarily the CliniMACS Prodigy® (Miltenyi Biotec GmbH, Germany) is used as a closed system. This system is disclosed in WO2009/072003. But it is not intended to restrict the use of the method of the present invention to the CliniMACS® Prodigy.

The terms "automated method" or "automated process" as used herein refer to any process being automated through the use of devices and/or computers and computer softwares which otherwise would or could be performed manually by an operator. Methods (processes) that have been automated require less human intervention and less human time to deliver. In some instances the method of the present invention is automated if at least one step of the present method is performed without any human support or intervention. Preferentially the method of the present invention is automated if all steps of the method as disclosed herein are performed without human support or intervention. Preferentially the automated process is implemented on a closed system such as CliniMACS® Prodigy as disclosed herein.

The term "therapeutic effective amount" means an amount, which provides a therapeutic benefit in a patient.

The term "marker" as used herein refers to a cell antigen that is specifically expressed by a certain cell type. Preferentially, the marker is a cell surface marker, so that enrichment, isolation and/or detection of living cells can be performed. The markers may be positive selection markers such as CD56 as used herein or may be negative selection markers such as CD140b, CD141, CD10 as used herein. Cell antigens that are expressed intracellularly, e.g. structural or muscle proteins or transcription factors are analytical markers used to identify cardiomyocytes and/or subpopulations thereof, but cannot be used for enrichment of viable cells.

The term "expression" as used herein refers interchangeably to expression of a gene or gene product, including the encoded protein. Expression of a gene product may be determined e.g. by an immunoassay using antibodies that bind with the protein. For example, a well-suited technology for determining the level of proteins, e.g. the cell surface proteins CD140b, CD141, CD10, CD56 is the flow cytometry technology.

Alternatively, expression of a gene may be determined by e.g. measurement of mRNA levels. The term "PSC-derived cardiomyocyte" or "PSC-derived cardiomyocytes" as used herein refers to sarcomere-containing striated muscle cells generated in vitro from pluripotent stem cells by inductive cues, e.g. special media, small molecules, growth factors, cytokines, overexpression of selected genes or RNAs. Cardiomyocytes are characterized by the expression of specialized molecules e.g. proteins like myosin heavy chain, Troponin T, myosin light chain, cardiac alpha-actinin. Cardiomyocytes can as well be generated from other cell types. The term "cardiomyocyte" as used herein is an umbrella term comprising any cardiomyocyte subpopulation or cardiomyocyte subtype, e.g. atrial, ventricular and pacemaker cardiomyocytes.

The term "non-cardiomyocyte" or "non-cardiomyocytes" as used herein refers to any cell or population of cells in a cell preparation not fulfilling the criteria of a "cardiomyocyte" as defined and used herein.

The terms "cardiomyocyte subpopulation" or "cardiomyocyte subtype" are used interchangeably and refer to any subpopulation within a population of cardiomyocytes as defined above. The respective cardiomyocyte subpopulation or subtype is identified by co-expression of selected cell surface markers with intracellular cardiomoycyte specific protein, like myosin heavy chain, troponin T, cardiac alpha actinin, myosin light chain. The cardiomyocytes and/or cardiomyocyte subpopulations obtainable by the methods disclosed herein may be used for subsequent steps such as research, diagnostics, pharmacological or clinical applications known to the person skilled in the art.

The term "cardiovascular cells" as used herein refer to cells of the cardiovascular lineage generated in vitro by differentiation of pluripotent stem cells. This includes but is not restricted to uni- or multipotent progenitor cells, smooth muscle cells, endothelial cells, fibroblasts, cardiomyocytes and respective subtypes of each cell-type.

The term "removal/depletion" as used herein refers to a process of a negative selection that separates desired cardiomyocytes from the undesired non-cardiomyocytes e.g. by labeling with antigen-binding molecules specific for non-cardiomyocytes as defined and used herein or by the use of physical depletion methods, e.g. Percoll gradient centrifugation or by the use of special media (e.g. glucose depleted lactate rich media) or by use of DNA or RNA molecules or molecular beacons thereby specifically labeling non-cardiomyocytes and enabling their depletion by a cell separation procedure, e.g. magnetic cell sorting or fluorescence activated cell sorting (e.g. FACS®).

The term "tag" as used herein refers to the coupling or conjugation of the antigen-binding molecule, e.g. an antibody or antigen binding fragment thereof, to other molecules, e.g. particles, fluorophores, haptens like biotin, or larger surfaces such as culture dishes and microtiter plates. In some cases the coupling results in direct immobilization of the antigen-binding molecule, e.g. if the antigen-binding molecule is coupled to a larger surface of a culture dish. In other cases this coupling results in indirect immobilization, e.g. an antigen-binding molecule coupled directly or indirectly (via e.g. biotin) to a magnetic bead is immobilized if said bead is retained in a magnetic field. In further cases the coupling of the antigen-binding molecule to other molecules results not in a direct or indirect immobilization but allows for enrichment, separation, isolation, and detection of cells according to the present invention, e.g. if the antigen-binding molecule is coupled to a fluorophore which then allows discrimination of stronger labeled cells, weaker labeled cells, and non-labeled cells, e.g. via flow cytometry methods, like FACSorting, or fluorescence microscopy.

The term "particle" as used herein refers to a solid phase such as colloidal particles, microspheres, nanoparticles, or beads. Methods for generation of such particles are well known in the field of the art. The particles may be magnetic particles. The particles may be in a solution or suspension or they may be in a state prior to use in the present invention. The lyophilized particle is then reconstituted in convenient buffer before contacting the sample to be processed regarding the present invention.

The term "magnetic" in "magnetic particle" as used herein refers to all subtypes of magnetic particles which can be prepared with methods well known to the skilled person in the art, especially ferromagnetic particles, superparamagnetic particles and paramagnetic particles. "Ferromagnetic" materials are strongly susceptible to magnetic fields and are capable of retaining magnetic properties when the field is removed. "Paramagnetic" materials have only a weak magnetic susceptibility and when the field is removed quickly lose their weak magnetism. "Superparamagnetic" materials are highly magnetically susceptible, i.e. they become strongly magnetic when placed in a magnetic field, but, like paramagnetic materials, rapidly lose their magnetism.

The term "antibody" as used herein refers to polyclonal or monoclonal antibodies, which can be generated by methods well known to the person skilled in the art. The antibody may be of any species, e.g. murine, rat, sheep, human. For therapeutic purposes, if non-human antigen binding fragments are to be used, these can be humanized by any method known in the art. The antibodies may also be modified antibodies (e.g. oligomers, reduced, oxidized and labeled antibodies).

The term "antibody" comprises both intact molecules and antibody fragments (antigen binding fragments), such as Fab, Fab', F(ab') 2, Fv and single-chain antibodies.

The linkage (coupling or conjugation) between antibody and tag or particle can be covalent or non-covalent. A covalent linkage can be, e.g. the linkage to carboxyl-groups on polystyrene beads, or to NH2 or SH2 groups on modified beads. A non-covalent linkage is e.g. via biotin-avidin or a fluorophore-coupled-particle linked to anti-fluorophore antibody. Methods for coupling antibodies to particles, fluorophores, haptens like biotin or larger surfaces such as culture dishes are well known to the skilled person in the art.

For removal, enrichment, isolation or selection in principle any sorting technology can be used. This includes for example affinity chromatography or any other antibody-dependent separation technique known in the art. Any ligand-dependent separation technique known in the art may be used in conjunction with both positive and negative separation techniques that rely on the physical properties of the cells.

An especially potent sorting technology is magnetic cell sorting. Methods to separate cells magnetically are commercially available e.g. from Invitrogen, Stem cell Technologies, in Cellpro, Seattle or Advanced Magnetics, Boston. For example, monoclonal antibodies can be directly coupled to magnetic polystyrene particles like Dynal M 450 or similar magnetic particles and used e.g. for cell separation. The Dynabeads technology is not column based, instead these magnetic beads with attached cells enjoy liquid phase kinetics in a sample tube, and the cells are isolated by placing the tube on a magnetic rack. However, in a preferred embodiment for enriching, sorting and/or detecting cardiomyocyte subpopulations from a sample containing cardiomyocytes according the present invention monoclonal antibodies are used in conjunction with colloidal superparamagnetic microparticles having an organic coating by e.g. polysaccharides (Magnetic-activated cell sorting (MACS®) technology (Miltenyi Biotec, Bergisch Gladbach, Germany)). These particles (nanobeads or MicroBeads) can be either directly conjugated to monoclonal antibodies or used in combination with anti-immunoglobulin, avidin or anti-hapten-specific MicroBeads. The MACS technology allows cells to be separated by incubating them with magnetic nanoparticles coated with antibodies directed against a particular surface antigen. This causes the cells expressing this antigen to attach to the magnetic nanoparticles. Afterwards the cell solution is transferred on a column placed in a strong magnetic field. In this step, the cells attach to the nanoparticles (expressing the antigen) and stay on the column, while other cells (not expressing the antigen) flow through. With this method, the cells can be separated positively or negatively with respect to the particular antigen(s). In case of a positive selection the cells expressing the antigen(s) of interest, which attached to the magnetic column, are washed out to a separate vessel, after removing the column from the magnetic field. In case of a negative selection the antibody used is directed against surface antigen(s), which are known to be present on cells that are not of interest.

After application of the cells/magnetic nanoparticles solution onto the column the cells expressing these antigens bind to the column and the fraction that goes through is collected, as it contains the cells of interest. As these cells are non-labeled by an antibody coupled to nanoparticles, they are "untouched". The procedure can be performed using direct magnetic labeling or indirect magnetic labeling. For direct labeling the specific antibody is directly coupled to the magnetic particle. Indirect labeling is a convenient alternative when direct magnetic labeling is not possible or not desired. A primary antibody, a specific monoclonal or polyclonal antibody, a combination of primary antibodies, directed against any cell surface marker can be used for this labeling strategy. The primary antibody can either be unconjugated, biotinylated, or fluorophore-conjugated. The magnetic labeling is then achieved with anti-immunoglobulin MicroBeads, anti-biotin MicroBeads, or anti-fluorophore MicroBeads. The method of the present invention allows for both the direct magnetic labeling and the indirect magnetic labeling with the aim of a) removal of non-cardiomyocytes from a mixed cell population or b) enrichment of cardiomyocytes and cardiomyocyte subtpyes from a mixed cell population. The above-described processes can also be performed in a closed cell sample processing system such as CliniMACS® (Miltenyi Biotec GmbH, Germany) or CliniMACS® Prodigy (Miltenyi Biotec GmbH, Germany).

The term "agent" as used herein refers to substances, e.g. small molecules, growth factors, cytokines, overexpression of selected genes or RNAs which are intended to add to a cell medium, preferentially directing the differentiation of pluripotent stem cells into cardiovascular cells, preferred cardiomyocytes.

The terms "substantially pure composition of cardiomyocytes" or "substantially pure composition of subpopulation of cardiomyocytes" as used herein refer to cell compositions containing at least 70%, more preferentially at least 90%, most preferentially at least 95% of alpha-actinin or troponin T or myosin heavy chain or myosin light chain positive cells in the target cell fraction.

The term "differentiation of pluripotent and/or multipotent stem cells into cardiomyocytes" includes any media or methods suitable for the differentiation of cardiomyocytes with efficacies of at least 20%, more preferentially at least 50%, most preferentially at least 70%. Such methods are well-known in the art such as disclosed e.g. in Zhang et al. (2015).

The enriched cardiomyocyte populations and/or subpopulations can also be used before and/or after cell culturing as a pharmaceutical composition in the therapy, e.g. cellular therapy, or prevention of diseases. The pharmaceutical composition may be transplanted into an animal or human, preferentially a human patient. The pharmaceutical composition can be used for the treatment and/or prevention of diseases in mammals, especially humans, possibly including administration of a pharmaceutically effective amount of the pharmaceutical composition to the mammal. The disease may be any disease, which can be treated and/or prevented through the presence of cardiomyocytes and/or through increasing the concentration of the relevant cells in/at the relevant place, i.e. the heart. The treated and/or preventively treated disease may be any heart disorder, e.g. a disorder characterized by loss of cardiomyocytes as a result of ischemia or acute/chronic inflammation. The treatment may be the transplantation of enriched cardiomyocyte populations and/or subpopulations to the relevant place of the heart. Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

EXAMPLES

Example 1: Differentiation of Pluripotent and/or Multipotent Stem Cells into Cardiomyocytes The protocol used for the highly efficient generation of pluripotent stem cell-derived cardiomyocytes was based on a previously published method by Zhang et al. (2015), combining Wnt signaling activators and inhibitors as well as FGF-2, Activin A, BMP-4 and a Rho-kinase inhibitor (FIG. 1A). Cardiomyocytes were generated with high efficacies within 7 days as shown by flow cytometry analysis of cardiac Troponin T (cTnT) expression (see FIG. 1B) and the typical morphology of PSC-derived cardiomyocyte cultures (see FIG. 1C).

Example 2: Identification of Cardiomyocyte and Non-Cardiomyocyte Markers Suitable for the Purification of PSC Derived Cardiomyocytes hESC and iPSC were differentiated according to a protocol described in Example 1. For the identification of cardiomyocyte and non-cardiomyocyte markers a flow cytometry based surface marker screen with >400 antibodies was performed in a 96 well format. Cells were counterstained with an antibody against intracellular cardiomyocyte marker such as Alpha actinin or TroponinT (cTNT) in order to distinguish between cardiomyocytes and non-cardiomyocytes. Inside stains were performed using the Inside Stain Kit® (Miltenyi Biotec). The outcome of the surface marker screen was analyzed using a Flow Cytometer e.g. MACSQuant® (Miltenyi Biotec). Using this procedure several markers were identified that showed either little or no co-expression with the intracellular cardiac marker (see FIGS. 2A and 2B), fully overlapped with the expression of the intracellular cardiomyocyte marker (see FIGS. 3A and 3B) or partially overlapped with the expression of the cardiac marker (See FIGS. 13A-F). The latter markers label cardiomyocyte subpopulations. Moreover, some surface markers that were previously described for non-cardiomyocytes were analyzed by this screening approach (see FIG. 4). Data indicate that non of the three markers only labels non-cardiomyocytes as all three markers show partial co-expression with the intracellular cardiac markers, Troponin T or Alpha actinin.

Example 3: Enrichment of PSC-Derived Cardiomyocytes by Magnetic Depletion of Non-Cardiomyocytes A PSC-derived cardiomyocyte culture (see Example 1) was used for magnetic activated cell sorting (MACS). Cells were subsequently labeled with an anti CD140b biotin antibody and an anti-biotin antibody conjugated to magnetic beads and further separated using a MACS cell separation column (Miltenyi Biotec) that was placed into a magnetic field of a MACS® Separator (Miltenyi Biotec). The negative fraction was counterstained with antiCD140b and the intracellular cardiomyocyte-specific marker cardiac TroponinT (cTNT). It was shown that the purity of the starting cardiomyocyte population could be increased from 37.1% to 48.18% (FIG. 5).

Example 4: Enrichment of PSC Derived Cardiomyocytes by Magnetic Enrichment of Cardiomyocytes A PSC-derived cardiomyocyte culture (see Example 1) was used for magnetic activated cell sorting (MACS). Cells were labeled with either antiSirpa biotin or antiVCAM-1 biotin antibodies and an anti-biotin antibody conjugated to magnetic beads. Both markers were previously described for enrichment of PSC-derived cardiomyocytes. Cells were further separated using a MACS cell separation column (Miltenyi Biotec) that was placed into a magnetic field of a MACS® Separator (Miltenyi Biotec). The positive fraction (enriched cardiomyocytes) was counterstained with either antiSirpa or antiVCAM-1 antibodies and antibodies against the intracellular cardiomyocyte-specific marker cardiac TroponinT (cTNT). It was shown that PSC-derived cardiomyocytes could be enriched from 17% to 32% using antiSirpa and from 12% to 34% using antiVCAM-1 as cell separation antibodies (See FIGS. 6A and 6B, respectively)

Figure 7:
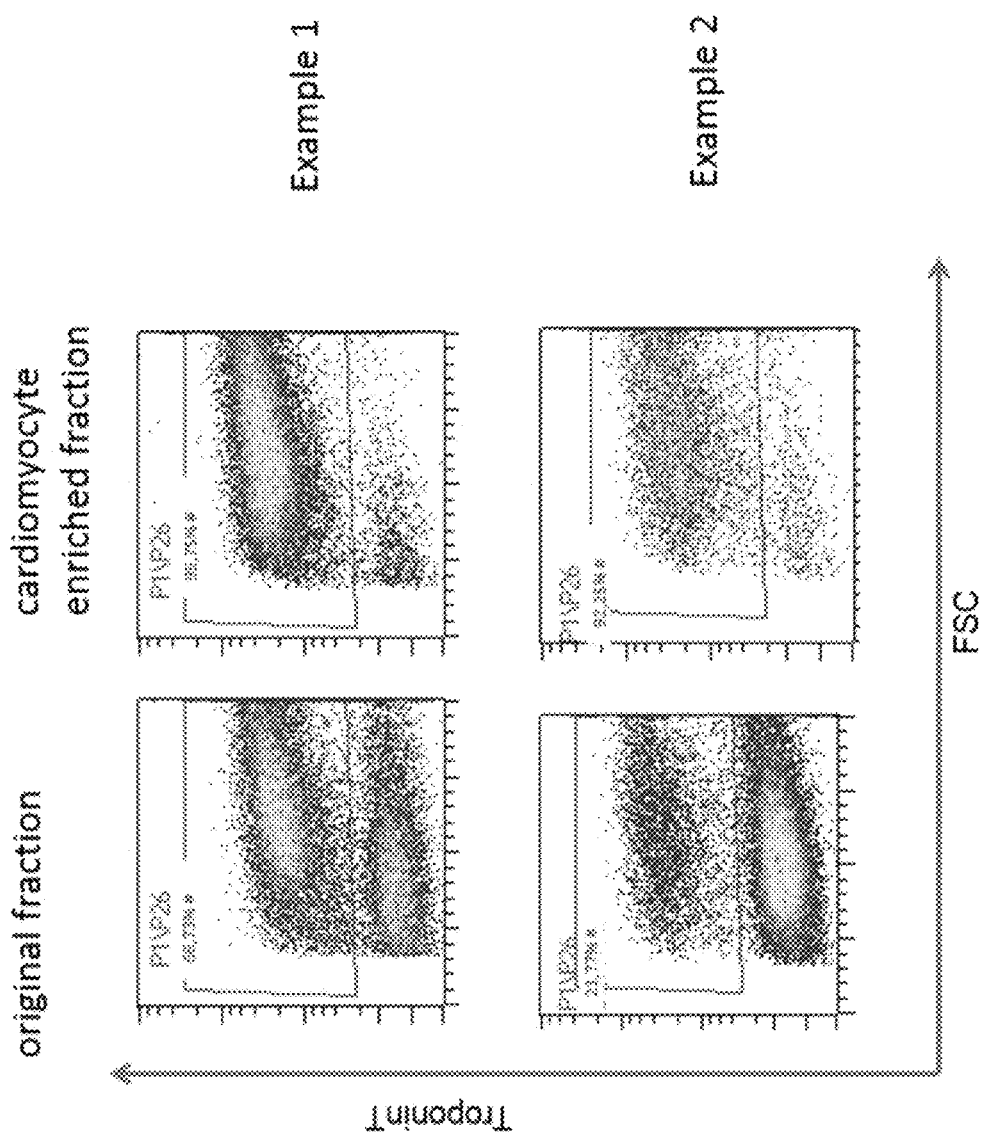

Example 5: Enrichment of PSC-Derived Cardiomyocytes Using a One or Two Step Cell Separation Strategy A PSC derived cardiomyocyte culture (see Example 1) was used for MACS. Depending on the differentiation efficiency and the stem cell clone a one or two-step cell separation strategy was used. The first step includes the magnetic labeling of the non-cardiomyocyte population with following antibodies antiCD140b biotin, antiCD10 biotin and antiCD141 biotin, a combination of antibodies specific for the non-cardiomyocyte population and an anti-biotin antibody conjugated to a magnetic bead. Cells were then separated using a MACS cell separation column (Miltenyi Biotec) that was placed into a magnetic field of a MACS® Separator (Miltenyi Biotec). The cardiomyocyte enriched fraction obtained after only depletion of non-cardiomyocytes contained either a highly purified cardiomyocyte population as shown in FIG. 7 or a partly purified cardiomyocyte population as shown in FIG. 8. In the latter result, cardiomyocytes were subsequently directly magnetically labeled using antiCD56 antibodies directly conjugated to magnetic beads (step 2). Cells were further separated using a MACS cell separation column (Miltenyi Biotec) that was placed into a magnetic field of a MACS® Separator (Miltenyi Biotec). The positive cardiomyocyte containing fraction showed high purities when counterstained with the antibodies against the cardiomyocyte marker cardiac TroponinT (cTNT).

Example 6: Enrichment of PSC-Derived Cardiomyocytes Using Fluorescence Activated Cell Sorting (FACS)

A PSC-derived cardiomyocyte culture (see Example 1) was used for FACS. Cells were stained using antiCD140b, antiCD10 and antiCD141 PE-Vio770 (Miltenyi Biotec) and antiCD56 VioBright™ FITC antibodies. Cells were then transferred into a sorting cartridge and sorted using the microchip based Flow Cytometer MACS QuantTyto® (Miltenyi Biotec). CD140b, CD10 and CD141 negative and CD56 positive cells were defined and sorted as positive fraction. Cells of the positive fraction were counterstained using the cardiac marker cardiac TroponinT, thus showing high purities of the positive fraction (see FIG. 9).

Example 7: Immunofluorescence Analysis of Non-Purified and Purified PSC Derived Cardiomyocytes The PSC-derived cardiomyocyte culture (Example 1) was purified using MACS as described in Example 5. Cells of the original fraction, the non-cardiomyocyte depleted fraction (Step 1) and the cardiomyocyte enriched fraction (Step 2) were plated in standard cultivation medium supplemented with StemMACS® Thiazovivin (Miltenyi Biotec) onto a matrigel (Corning) coated 96 well plate. The cell density was 300.000 cells/cm². Cells were cultured for 24 h at 37° C. and 5% $CO_2$. Afterwards cells were fixed using 4% PFA. The blocking was performed using autoMACS® rinsing buffer supplemented with MACS® BSA stock solution (Miltenyi Biotec). Cells were then stained using cardiac TroponinT antibodies (Miltenyi Biotec) anti human IgG Alexa488 (Life Technologies) and Hoechst using components of the Inside Stain Kit® (Miltenyi Biotec). As shown in FIGS. 10A-C the stepwise purification process of PSC-derived cardiomyocytes could be visualized using a fluorescence microscope.

Example 8: Functionality and Morphology of Purified Cardiomyocytes

The PSC-derived cardiomyocyte culture (Example 1) was purified using MACS as described in Example 5. Cells of the positive fraction were plated in standard cultivation medium supplemented with StemMACS® Thiazovivin (Miltenyi Biotec) onto a Matrigel® (Corning) coated 96 well plate. The cell density was 300.000 cells/cm². Cells were cultured for 24 h at 37° C. and 5% $CO_2$. Then cell morphology was monitored (see FIG. 11B). Cells were then live stained using the calcium sensitive dye Flou8 (Life Technologies) in order to visualize the calcium fluxes of cardiomyocytes. Cardiomyocyte-typical calcium fluxes were observed using a fluorescence microscope (see FIG. 11A).

Example 9: Analysis of Cardiomyocyte Specific Makers of Purified Cardiomyocytes

The PSC-derived cardiomyocyte culture (Example 1) was purified using MACS as described in Example 5. The purified cardiomyocyte fraction was stained with different combinations of antibodies against cardiomyocyte specific intracellular markers using the Inside Stain Kit® (Miltenyi Biotec) and analyzed using a Flow Cytometer such as the MACSQuant® (Miltenyi Biotec). The marker combinations showed cardiomyocyte specific expression profiles (see FIG. 12).

Figure 2A:
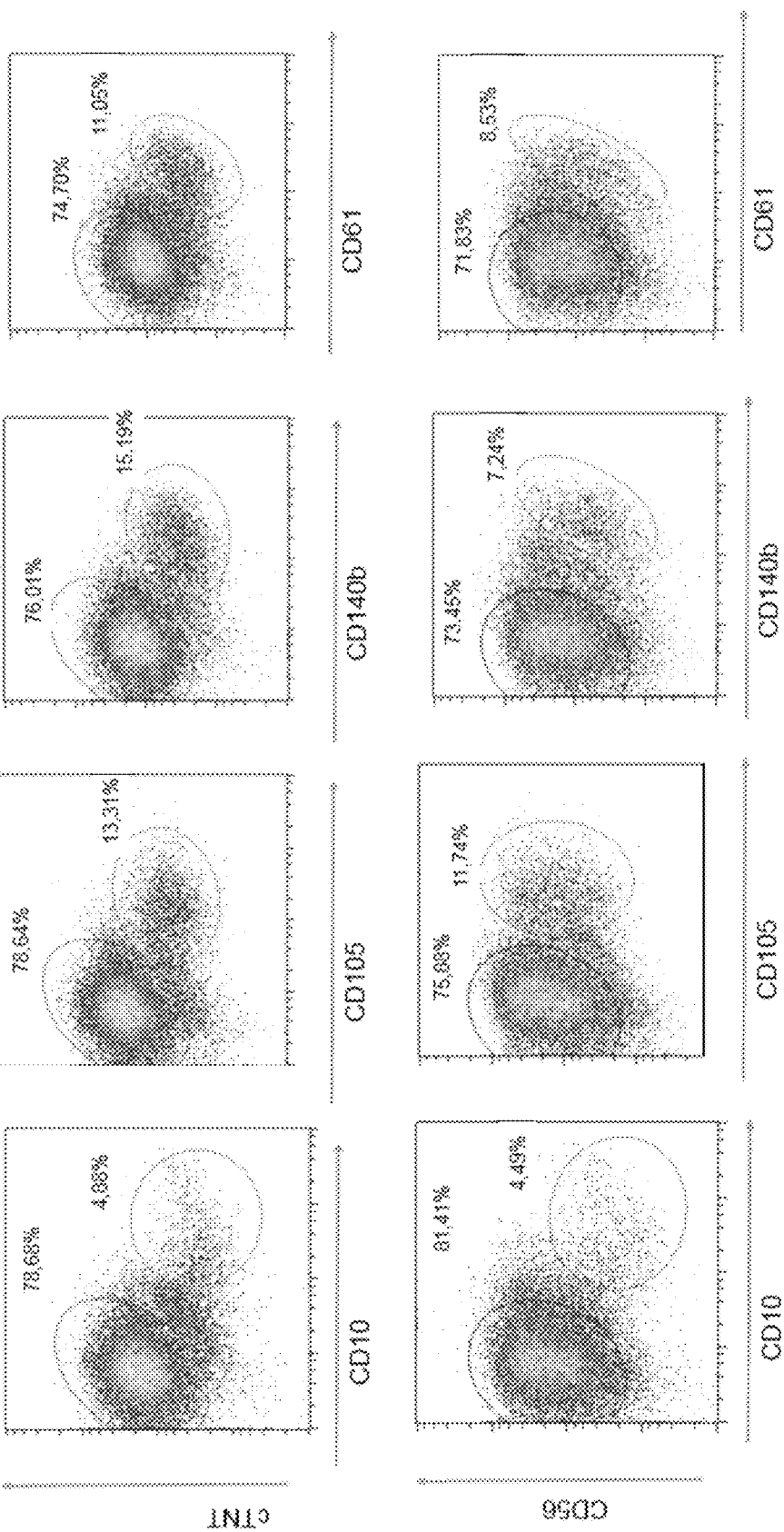
FIGS. 2A-B A flow cytometry-based antibody screening identified several surface markers of non-cardiomyocytes as indicated by little or no overlap of expression with the CM markers Alpha actinin or Troponin T. Moreover, these markers show co-expression with CD56. Dot Plots of respective markers are shown in this figure (FIGS. 2A, 2B).
Figure 2B:
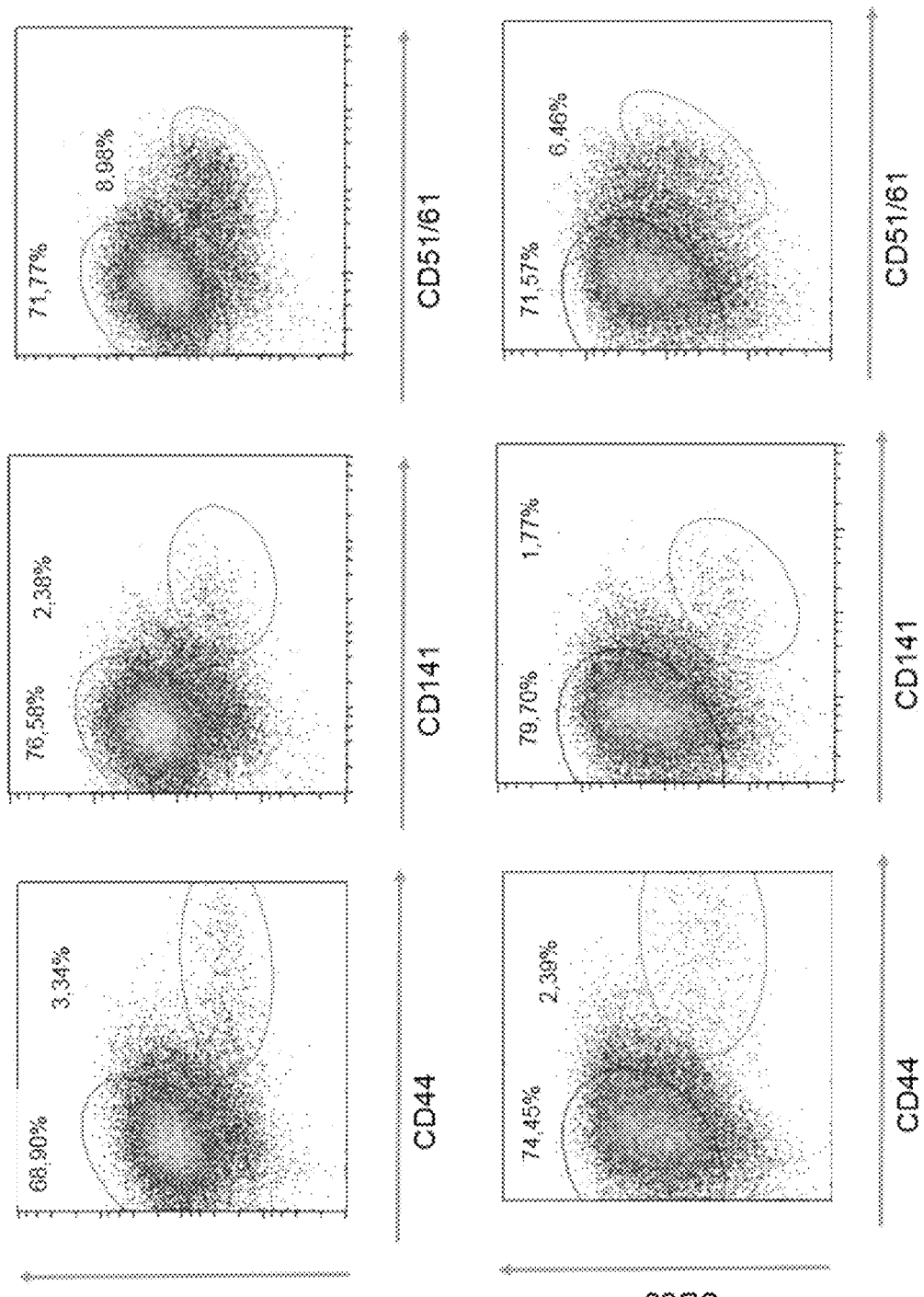
Figure 3A:
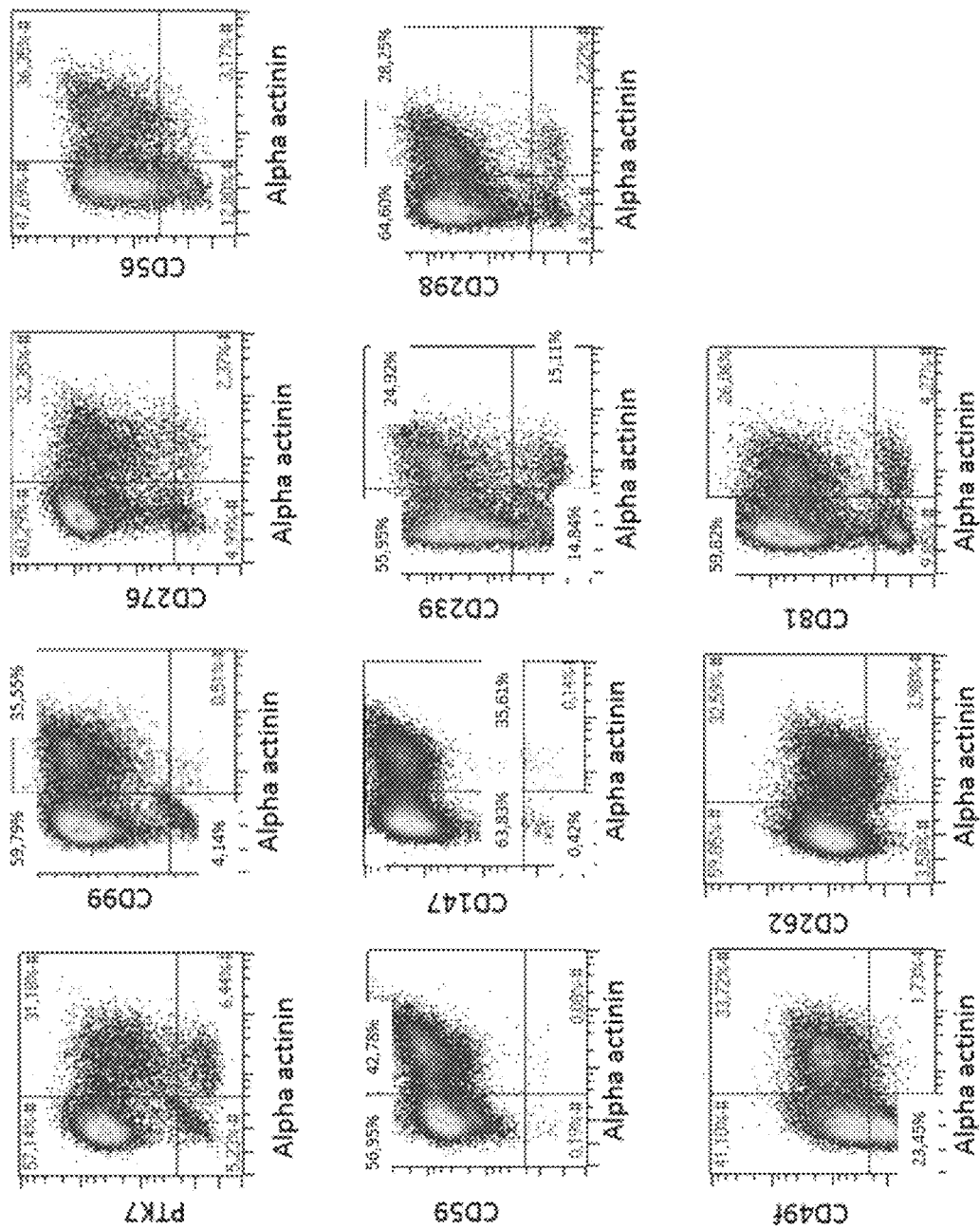
FIGS. 3A-B A flow cytometry-based antibody screening identified several surface markers of cardiomyocytes as indicated by overlapping expression of respective surface markers with the CM markers Alpha actinin or Troponin T. Dot Plots of respective markers are shown in this figure (FIG. 3A, FIG. 3B).
Figure 3B:
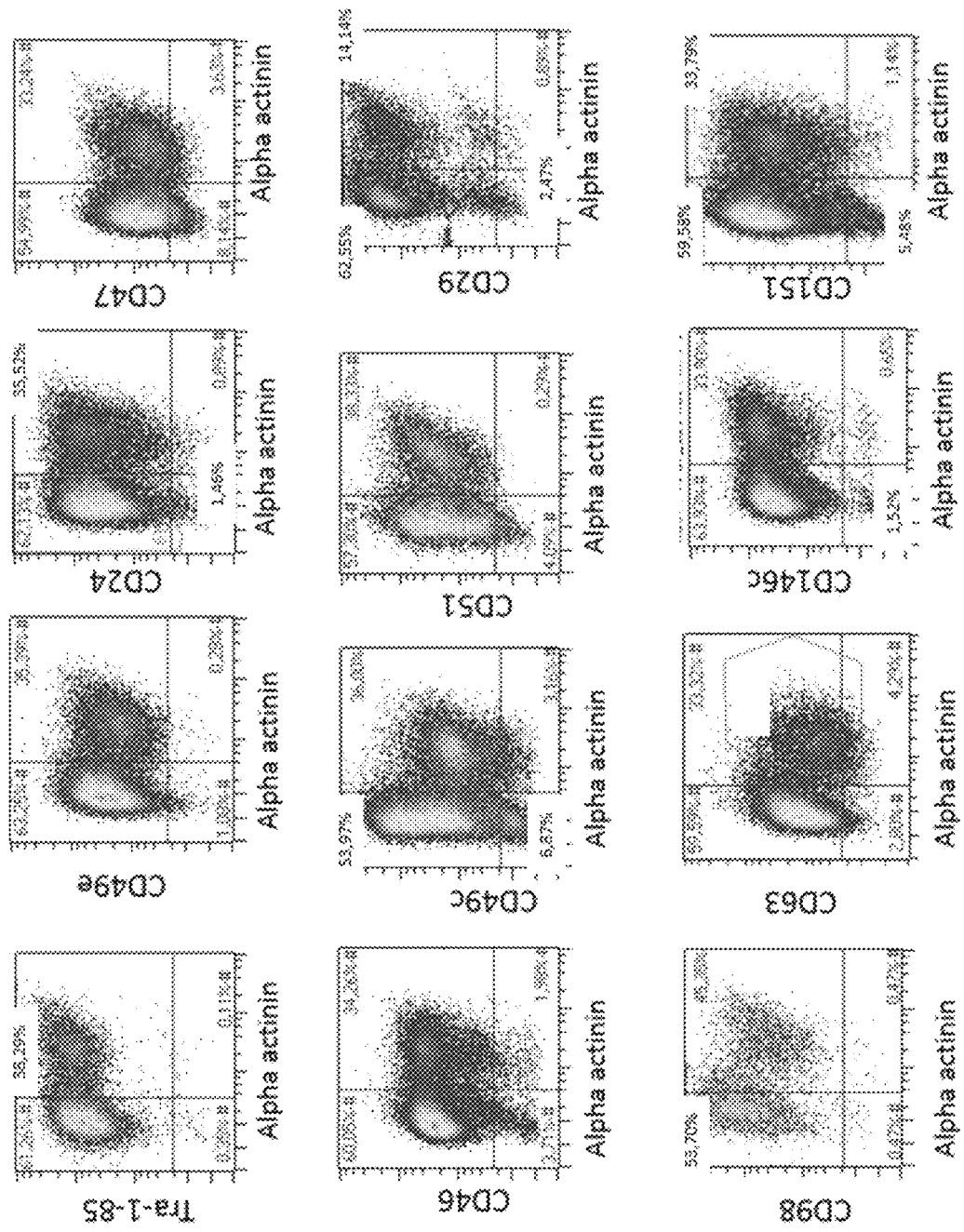

Example 10: Identification of Suitable Marker Combinations for Cardiomyocyte Purification Marker combinations out of 8 non-cardiac markers were co-stained with CD56 and cardiac TroponinT, an intracellular cardiac marker, in order to find specific combinations, that can be used for sorting strategies. To that end frozen iPS derived cardiomyocytes (day 8) were thawed in standard cultivation medium. 2×10E5 cells per well were then added to a 96 well plate containing specific antibodies of the marker combinations in APC and CD56 in FITC. Surface markers were stained using a standard protocol for flow cytometry. Cardiac muscle structures (cardiac TroponinT) were then stained using the inside stain kit (Miltenyi Biotec). Cell stainings were analyzed using the MACS Quant Analyzer (Miltenyi Biotec). All single marker stainings showed partial overlap with the non-myocyte population (FIGS. 2A and 2B). Non-cardiomyocytes and cardiomyocytes could not be clearly distinguished. For that reason these single markers were not suitable for the efficient purification of PSC-derived cardiomyocytes. After cell sorting, remaining non cardiomyocytes would contaminate the cardiomyocyte population. In contrast to that the number of labeled non-myocytes could be increased by combining at least two of the non-cardiomyocyte markers (FIGS. 14A-F). Cardiomyocyte and non-cardiomyocyte populations could be clearly distinguished. Therefore, these markers allow for highly efficient purification of the cardiomyocyte population as shown in FIGS. 7-9.

REFERENCES

Burridge et al., 2014. Chemically defined generation of human cardiomyocytes. Nat Methods 11:855-60

Dubois et al., 2011. SIRPA is a specific cell-surface marker for isolating cardiomyocytes derived from human pluripotent stem cells. Nat Biotechnol. 29:1011-8.

Fuerstenau-Sharp et al., 2015. Generation of highly purified human cardiomyocytes from peripheral blood mononuclear cell-derived induced pluripotent stem cells. PloS One. 10(5): e0126596

Piccini et al., 2015. Human pluripotent stem cell-derived cardiomyocytes: Genome-wide expression profiling of long-term in vitro maturation in comparison to human heart tissue. Genom Data 4:69-72

Skelton et al., 2016. CD13 and ROR2 Permit Isolation of Highly Enriched Cardiac Mesoderm from Differentiating Human Embryonic Stem Cells. Stem Cell Reports. 12; 6:95-108.

Tohyama et al., 2013. Distinct metabolic flow enables large-scale purification of mouse and human pluripotent stem cell-derived cardiomyocytes. Cell Stem Cell. 12(1):127-37.

Uosaki et al., 2011. Efficient and scalable purification of cardiomyocytes from human embryonic and induced pluripotent stem cells by VCAM1 surface expression. PloS One. 6(8): e23657.

Van den Berg et al., 2015. Transcriptome of human foetal heart compared with cardiomyocytes from pluripotent stem cells. Development 142:3231-8.

Xu et al., 2008. Highly enriched cardiomyocytes from human embryonic stem cells. Cytotherapy. 10(4):376-89

Zhang et al., 2015. Universal cardiac induction of human pluripotent stem cells in two and three-dimensional formats: implications for in vitro maturation. Stem Cells; 33:1456-69.

The invention claimed is:

1. A method for generation, isolation, detection and/or analysis of cardiomyocytes derived from a starting cell composition comprising pluripotent and/or multipotent stem cells, the method comprising the steps
    a) differentiating said pluripotent and/or multipotent stem cells into cardiovascular cells, thereby generating a sample comprising cardiomyocytes and non-cardiomyocytes;
    b) labeling the non-cardiomyocytes of said sample with three antibodies or antigen binding fragments thereof specific for antigens of non-cardiomyocytes, wherein said three antibodies or antigen binding fragments are antiCD10, antiCD140b, and antiCD1414; and
    c) depleting said labeled non-cardiomyocytes from said sample.

2. The method according to claim 1, wherein said three antibodies or antigen binding fragments thereof specific for antigens of non-cardiomyocytes are coupled to a tag.

3. The method according to claim 2, wherein the depletion step c) is performed by magnetic cell separation and said tag is a magnetic particle or by fluorescence-activated cell sorting and said tag is a fluorophore.

4. The method according to claim 1, wherein the method further comprises the steps:
d) labeling the cardiomyocytes of said sample after step c) with at least one antibody or antigen binding fragment thereof specific for antigens of cardiomyocytes, wherein said at least one antibody or antigen binding fragment thereof is selected from the group consisting of antiPTK7, antiCD99, antiCD276, antiCD56, antiCD59, antiCD147, antiCD239, antiCD298, antiCD49f, antiCD262, antiCD81, antiTra-1-85, antiCD49e, antiCD24, antiCD47, antiCD46, antiCD49c, antiCD51, antiCD29, antiCD98, antiCD63, and antiCD146c, and antiCD151; and
e) enriching said labeled cardiomyocytes.

5. The method according to claim 4, wherein said at least one antibody or fragment thereof specific for cardiomyocytes is antiCD56.

6. The method according to claim 4, wherein said at least one antibody or fragment thereof specific for antigens of cardiomyocytes is coupled to a tag.

7. The method according to claim 6, wherein the enrichment step e) is performed by magnetic cell separation and said tag is a magnetic particle or by fluorescence-activated cell sorting and said tag is a fluorophore.

8. The method according to claim 7, wherein the magnetic particle coupled to three antibodies or antigen binding fragments thereof specific for antigens of non-cardiomyocytes and the magnetic particle coupled to said at least one antibody or fragment thereof specific for antigens of cardiomyocytes are distinguishable magnetic particles if the labeling of the non-cardiomyocytes in step b) and the labeling of the cardiomyocytes in step d) is performed simultaneously or wherein the fluorophore coupled to said three antibodies or antigen binding fragments thereof specific for antigens of non-cardiomyocytes and the fluorophore coupled to said at least one antibody or fragment thereof specific for antigens of cardiomyocytes are distinguishable fluorophores if the labeling of the non-cardiomyocytes in step b) and the labeling of the cardiomyocytes in step d) is performed simultaneously.

9. The method of claim 1, wherein the method after step c) comprises the additional steps:
I) labeling the cardiomyocytes of step c) with at least one antibody or antigen binding fragment thereof specific for the antigens of a subpopulation of cardiomyocytes, wherein said at least one antibody or antigen binding fragment thereof is selected from the group consisting of antiPTK7, antiCD81, antiCD276, antiCD239, antiCD298, antiCD49c, antiCD200, antiCD230, antiCD324, antiROR1, antiCD146, antiCD317, antiCD49a, antiCD43, antiCD111, antiCD201, antiCD138, antiCD271, antiCD222, antiCD82, antiCD44, antiCD90, antiCD95, antiCD142, anti-Notch-2, antiKIR-2D, antiCD197, antiCD240DCE, antiCD184, antiASCA-1 (GLAST), antiCCR10, anti-CDIR, antiCD183, antiCD97, antiCD49b, antiCD134, antiCD13, antifMLP, antiCD83, antiCD79b, antiCD5, antiCD74, and antiCD80; and
II) enriching said labeled cardiomyocytes of step I), thereby enriching a subpopulation of cardiomyocytes.

10. The method of claim 4, wherein the method after step e) comprises the additional steps:
I) labeling the cardiomyocytes of step e) with at least one antibody or antigen binding fragment thereof specific for the antigens of a subpopulation of cardiomyocytes, wherein said at least one antibody or antigen binding fragment thereof is selected from the group consisting of antiPTK7, antiCD81, antiCD276, antiCD239, antiCD298, antiCD49c, antiCD200, antiCD230, antiCD324, antiROR1, antiCD146, antiCD317, antiCD49a, antiCD43, antiCD111, antiCD201, antiCD138, antiCD271, antiCD222, antiCD82, antiCD44, antiCD90, antiCD95, antiCD142, anti-Notch-2, antiKIR-2D, antiCD197, antiCD240DCE, antiCD184, antiASCA-1 (GLAST), antiCCR10, anti-CDIR, antiCD183, antiCD97, antiCD49b, antiCD134, antiCD13, antifMLP, antiCD83, antiCD79b, antiCD5, antiCD74, and antiCD80; and
II) enriching said labeled cardiomyocytes of step I), thereby enriching a subpopulation of cardiomyocytes.

11. The method according to claim 1, wherein said method is performed in a closed system.

* * * * *